United States Patent [19]
Langer et al.

[11] Patent Number: 6,004,534
[45] Date of Patent: *Dec. 21, 1999

[54] TARGETED POLYMERIZED LIPOSOMES FOR IMPROVED DRUG DELIVERY

[75] Inventors: Robert S. Langer, Newton, Mass.; Hongming Chen, Lansdale, Pa.

[73] Assignee: Massachusetts Institute of Technology, Cambridge, Mass.

[*] Notice: This patent is subject to a terminal disclaimer.

[21] Appl. No.: 08/844,137

[22] Filed: Apr. 18, 1997

Related U.S. Application Data

[63] Continuation of application No. 08/786,617, Jul. 17, 1997, Pat. No. 5,762,904, which is a continuation of application No. 08/096,689, Jul. 23, 1993, abandoned.

[51] Int. Cl.$^6$ .......................... A61K 9/127; A61K 39/00; A61K 49/00
[52] U.S. Cl. .......................... 424/9.321; 264/4.1; 264/4.3; 424/9.4; 424/9.51; 424/9.52; 424/184.1; 424/278.1; 424/450; 424/812; 428/402.2
[58] Field of Search .................... 424/450, 1.21, 424/9.321, 9.51, 184.1, 812, 9.4; 428/402.2; 264/4.1, 4.3

[56] References Cited

U.S. PATENT DOCUMENTS

| Number | Date | Name | Class |
|---|---|---|---|
| 4,201,767 | 5/1980 | Fullerton et al. | 424/450 |
| 4,229,360 | 10/1980 | Schneider et al. | 264/4.6 |
| 4,348,329 | 9/1982 | Chapman | 554/80 |
| 4,429,008 | 1/1984 | Martin et al. | 428/402.2 |
| 4,485,045 | 11/1984 | Regen | 264/4.6 X |
| 4,522,811 | 6/1985 | Eppstein et al. | 514/2 |
| 4,560,599 | 12/1985 | Regen | 428/36 |
| 4,564,475 | 1/1986 | Masaichiro | 554/3 |
| 4,574,193 | 3/1986 | Regen . | |
| 4,587,055 | 5/1986 | Regen . | |
| 4,594,193 | 6/1986 | Regen | 554/81 |
| 4,652,257 | 3/1987 | Chang | 604/52 |
| 4,728,575 | 3/1988 | Gamble et al. | 428/402.2 |
| 4,753,788 | 6/1988 | Gamble | 424/450 X |
| 4,808,480 | 2/1989 | Regen | 428/402.2 |
| 4,847,080 | 7/1989 | Neurath et al. | 424/189.1 X |
| 4,861,521 | 8/1989 | Suzuki et al. | 554/80 |
| 4,877,501 | 10/1989 | Schnur et al. | 264/4.1 X |
| 4,877,619 | 10/1989 | Richer | 424/450 |
| 4,880,635 | 11/1989 | Janoff et al. | 424/450 |
| 4,900,556 | 2/1990 | Wheatley et al. | 424/450 |
| 4,925,661 | 5/1990 | Huang | 424/450 X |
| 4,933,114 | 6/1990 | O'Brien et al. | 554/80 |
| 4,935,171 | 6/1990 | Bracken | 264/4.6 |
| 4,975,282 | 12/1990 | Cullis et al. | 424/450 |
| 4,976,968 | 12/1990 | Steiner et al. | 424/491 |
| 4,990,291 | 2/1991 | Schoen et al. | 464/4.7 |
| 5,000,960 | 3/1991 | Wallach | 424/450 |
| 5,004,566 | 4/1991 | Schnur et al. | 554/80 |
| 5,061,484 | 10/1991 | Heldebrant | 514/832 X |
| 5,104,736 | 4/1992 | Wallach | 428/402.2 |
| 5,106,740 | 4/1992 | Hasegawa et al. | 424/450 |
| 5,158,769 | 10/1992 | Neurath et al. | 424/189.1 |
| 5,160,740 | 11/1992 | Hasegawa et al. | 424/450 |
| 5,198,224 | 3/1993 | Ono et al. | 424/450 |
| 5,204,096 | 4/1993 | Neurath et al. | 424/450 |
| 5,230,899 | 7/1993 | Park et al. | 424/450 |
| 5,258,499 | 11/1993 | Konigsberg et al. | 424/450 X |
| 5,366,881 | 11/1994 | Singh et al. | 424/450 X |
| 5,382,435 | 1/1995 | Geary et al. | 424/489 |
| 5,425,993 | 6/1995 | Morancais et al. | 428/402.24 |
| 5,464,630 | 11/1995 | Six et al. | 424/450 |
| 5,505,967 | 4/1996 | Geary et al. | 424/497 |
| 5,571,718 | 11/1996 | Dunn et al. | 435/252.3 |
| 5,762,904 | 6/1998 | Okada et al. | 424/1.21 |

FOREIGN PATENT DOCUMENTS

| Number | Date | Country |
|---|---|---|
| 0333523 | 9/1989 | European Pat. Off. . |
| 60-081192 | 5/1985 | Japan . |
| WO 90/06430 | 11/1990 | WIPO . |
| WO 90/06433 | 11/1990 | WIPO . |
| WO 92/04009 | 3/1992 | WIPO . |
| WO 93/10763 | 6/1993 | WIPO . |
| WO 95/03035 | 2/1995 | WIPO . |
| WO 95/04524 | 2/1995 | WIPO . |
| WO 96/13250 | 5/1996 | WIPO . |

OTHER PUBLICATIONS

Heath et al., 1981, "Covalent Attachment of Immunoglogulins to Liposomes Via Glycosphingolipids" Biochemica et Biophysica Acta 640:66–81.

Choi and Hahn, 1992, "Polymer–Coated Liposomes for Oral Drug Delivery", Yakche Hakhoechi 22:211–217 (Chem. Abstr. 118:407, Abstr. No. 197902e, 1993).

Okada et al., 1993, "Polymerized Liposomes for Oral Drug Delivery", Proc. Int. Symp. Controlled Release Bioact. Mater. pp. 302–303.

Patel et al., 1976, "Oral Administration of Insulin by Encapsulation within Liposomes", FEBS Lett. 62:60–63.

Regen, 1984, "Polymerized Vesicles", Polymer News 10:68–73.

Regen, 1987, "Polymerized Liposomes" *Liposomes: From Biophysics to Therapeutics* (Marcel Dekker, Inc., New York) pp. 73–109.

Skoza et al., 1978, "Procedure for Preparation of Liposomes with Large Internal Aqueous Space and High Capture by Reverse–phase Evaporation", Proc. Natl. Acad. Sci. USA 75:4194–4198.

Chen, 1996, *Polymerized Liposomes as Potential Oral Vaccine Delivery Vehicles*, (Doctoral Thesis, Massachusettes Institute of Technology).

(List continued on next page.)

*Primary Examiner*—Richard D. Lovering
*Attorney, Agent, or Firm*—Pennie & Edmonds LLP

[57] ABSTRACT

The present invention relates to targeted polymerized liposomes for oral and/or mucosal delivery of vaccines, allergens and therapeutics. In particular, the present invention relates to polymerized liposomes which have been modified on their surface to contain a molecule or ligand which targets the polymerized liposome to a specific site or cell type in order to optimize the immune response to the encapsulated antigen or the efficacy of the encapsulated drug.

18 Claims, 9 Drawing Sheets

OTHER PUBLICATIONS

Chen et al., 1996, "Polymerized Liposomes as Potential Oral Vaccine Carriers: Stability and Bioavailability", J. Controlled Release 42;263–272.

Chen et al., 1996, "Lectin–Bearing Polymerized Liposomes as Potential Oral Vaccine Carriers", Pharm. Res. 13:1378–1383.

Chen et al., 1996, "Surface–Modified Polymerized Liposomes: Novel Vehicles for Oral Vaccination", Proc. 5th World Congress of Chemical Engineering, pp. 824–829.

Ivanoff et al., 1996, "Mucosal Vaccination Against Schistosomiasis Using Liposome–Associated Sm 28 kDa Glutathione S–Transferase", Vaccine 14:1123–1131.

Chen et al., 1995, "Lectin–Bearing Polymerized Liposomes as Potential Oral Vaccine Carriers", Proc. Int. Symp. Controlled Release Bioact. Mater. 22:204–205 (CA: 123(26):350120y).

Chen and Langer, 1995, "Lectin–Bearing Polymerized Liposomes: Novel Vehicles for Oral Vaccine Delivery", Proc. 3rd U.S.–Japan Symposium on Drug Delivery, p. 23.

de Haan et al., 1995, "Mucosal Immunoadjuvant Activity of Liposomes: Induction of Systemic IgG and Secretory IgA Responses in Mice by Intranasal Immunization with an Influenza Subunit Vaccine and Coadministered Liposomes", Vaccine 13:155–162.

Estrada et al., 1995, "Intestinal Immunization of Mice with Antigen Conjugated to Anti–MHC Class II Antibodies", Vaccine 13:901–907.

Kilpatrick, 1995, "Lectins in Immunology", in: *Lectins: Biomedical Perspectives*, Pusztai and Bardocz, eds., Taylor & Francis, London, England, pp. 155–182.

Ogawa et al., 1995, "Oral Immunoadjuvant Activity of Lipophilic Derivatives of N–acetylglucosaminyl–β(1→4)–N–acetylmuramyl–L–alanyl–D–isoglutaminyl–(L)–2, 6–meso–diaminopimeric acid–(D)–amide", *Vaccine* 13:887–889.

Okada et al., 1995, "In Vitro Evaluation of Polymerized Liposomes as Oral Drug Delivery System", Pharm. Res. 12:576–582.

Zhou et al., 1995, "Mucosal IgA Response to Rectally Administered Antigen Formulated in IgA–Coated Liposomes", *Vaccine* 13:637–644.

Allen et al., 1994, "Antibody–Mediated Targeting of Long Circulating (Stealth®) Liposomes", J. Liposome Res. 4:1–25.

Anderson et al., 1994, "Cytokines in Liposomes: Preliminary Studies with IL–1, IL–2, IL–6, GM–CSF and Interferon–γ", Cytokine 6:92–101.

Aramaki et al., 1994, "Activation of Systemic and Mucosal Immune Response Following Nasal Administration of Liposomes", Vaccine 12:1241–1245.

Childers and Michalek, 1994, "Liposomes", pp. 241–254, in: *Novel Delivery Systems for Oral Vaccines*, O'Hagan, ed., CRC Press.

Lehr, 1994, "Bioadhesion Technologies for the Delivery of Peptide and Protein Drugs to the Gastrointestinal Tract", Critical Reviews in Therapeutic Drug Carrier Systems 11:119–160.

Lipford et al., 1994, "Vaccination with Immunodominant Peptides Encapsulated in Quil A–Containing Liposomes Induces Peptide–Specific Primary CD8+ Cytotoxic T Cells", Vaccine 12:73–80.

O'Hagan, 1994, "Microparticles as Oral Vaccines", in: *Novel Delivery Systems for Oral Vaccines*, O'Hagan, ed., CRC Press, Boca Raton, FL, pp. 175–204.

Russel–Jones, 1994, "Oral Vaccination with Lectins and Lectin–Like Molecules", in: *Novel Delivery Systems for Oral Vaccines*, O'Hagan, ed., CRC Press, Boca Raton, FL, pp. 225–254.

Tanguay et al., 1994, "In Vivo Modulation of Macrophage Tumoricidal Activity by Oral Administration of the Liposome–Encapsulated Macrophage Activator CGP 19835A", Cancer Res. 54:5882–5888.

Aramaki et al., 1993, "Stability of Liposomes In Vitro and Their Uptake by Rat Peyer's Patches Following Oral Administration", Pharm. Res. 10:1228–1231.

Clarke and Stokes, 1992, "The Intestinal and Serum Humoral Immune Response of Mice to Systemically and Orally Administered Antigens in Liposomes: I. The Response to Liposome–Entrapped Soluble Proteins", Vet. Immunol. Immunopathol. 32:125–138.

Clarke and Stokes, 1992, "The Intestinal and Serum Humoral Immune Response of Mice to Orally Administered Antigens in Liposomes: II. The Response to Liposome–Entrapped Bacterial Proteins", Vet. Immunol. Immunopathol. 32:139–148.

Tsuchida et al., 1992, "Polymerization of Unsaturated Phospholipids as Large Unilamellar Liposomes at Low Temperature", Macromolecules 25:207–212.

Uwiera et al., 1992, "Liposomes Targeted to Deliver Antisecretory Agents to Jejunal Mucosa", Can. J. Vet. Res. 56:249–255.

Childers et al., 1990/1991, "Mucosal and Systemic Responses to an Oral Liposome *Streptococcus mutans* Carbohydrate Vaccine in Humans", Regional Immunol. 3:289–296.

Childers, et al., 1990, "Ultrastructural Study of Liposome Uptake by M Cells of Rat Peyer's Patch: An Oral Vaccine System for Delivery of Purified Antigen", Regional Immunol. 3;8–16.

Eldridge et al., 1990, "Controlled Vaccine Release in the Gut–Associated Lymphoid Tissues. I. Orally Administered Biodegradable Microspheres Target the Peyer's Patches", J. Controlled Release 11:205–214.

Gregoriadis, 1990, "Immunological Adjuvants: A Role for Lipsomes", Immunol. Today 11:89–97.

Michalek et al., 1989, "Liposomes as Oral Adjuvants", Curr. Topics in Microbiol. and Immunol. 146:51–58.

Freeman and Chapman, 1988, "Polymerizable Liposomes: Applications in Biology and Medicine", in: *Liposomes as Drug Carriers* Gregoriadis, ed., John Wiley & Sons, pp. 821–839.

Kimura, 1988, "Transmucosal Passage of Liposomal Drugs", in: *Liposomes as Drug Carriers* Gregoriadis, ed., John Wiley & Sons, pp. 635–647.

Barbour et al., 1987, "Protection and Immunity in Commercial Chicken Layers Administered *Mycoplasma gallisepticum* Liposomal Bacterins", Avian Diseases 31:723–729.

Neutra et al., 1987, "Transport of Membrane–Bound Macromolecules by M Cells in Follicle–Associated Epithelium of Rabbit Peyer's Patch", Cell Tissue Res. 247:537–546.

Ogawa et al., 1986, "Enhancement of Serum Antibody Production in Mice by Oral Administration of Lipophilic Derivatives of Muramylpeptides and Bacterial Lipopolysaccharides with Bovine Serum Albumin", Meth. and Find. Exptl. Clin. Pharmacol. 8:117–125.

Weissig et al., 1986, "A New Hydrophobic Anchor for the Attachment of Proteins to Liposomal Membranes", FEBS Lett. 202:86–90.

O'Connor et al., 1985, "Bile Salt Damage of Egg Phosphatidylcholine Liposomes", Biochim. Biophys. Acta 817:95–102.

Regen, 1985, "Polymerized Phosphatidylcholine Vesicles as Drug Carriers", Ann. N.Y. Acad. Sci. 446:296–307.

Woodley, 1985, "Liposomes for Oral Administration of Drugs", CRC Crit. Rev. in Therapeutic Drug Carrier Systems 2:1–18.

Dorn et al., 1984, "Permeability Characteristics of Polymeric Bilayer Membranes from Methacryloyl and Butadiene Lipids", J. Am. Chem. Soc. 106:1627–1633.

Deshmukh et al., 1981, "Can Intact Liposomes Be Absorbed in the Gut?", Life Sci. 28:239–242.

Gros et al., 1981, "Polymeric Antitumor Agents on a Molecular and on a Cellular Level?", Angew. Chem. Int. Ed. Engl. 20:305–325.

Hupfer et al., 1981, "Polyreactions in Oriented Systems, 21; Polymeric Phospholipid Monolayers", Makromol. Chem. 182:247–253.

Weingarten et al., 1981, "Oral Ingestion of Insulin Liposomes: Effects of the Administration Route", Life Sci. 28:2747–2752.

Regen et al., 1980, "Polymerized Vesicles", J. Am. Chem. Soc. 102:6638–6640.

Rowland and Woodley, 1980, "The Stability of Liposomes In Vitro to pH, Bile Salts and Pancreatic Lipase", Biochim. Biophys. Acta 620:400–409.

Ostro:*Liposomes from Biophysics to Therapeutics*, Marcel Dekker, Inc., New York (1987), pp. 73–109, 165.

TARGETED POLYMERIZED LIPOSOMES FOR IMPROVED DRUG DELIVERY

This application is a continuation of Ser. No. 08/786,617, filed Jul. 17, 1997 and now U.S. Pat. No. 5,762,904, which in turn is a continuation of application Ser. No. 08/096,689, filed Jul. 23, 1993, now abandoned, both of which are incorporated herein by reference in their entirety.

This invention was made with government support under grant number SNIH-5R01-GM26698 and HD29129 awarded by the National Institutes of Health. The government has certain rights in the invention.

1. INTRODUCTION

The present invention relates to targeted polymerized liposomes for oral and/or mucosal delivery of vaccines, allergens and therapeutics. In particular, the present invention relates to polymerized liposomes which have been modified on their surface to contain a molecule or ligand which targets the polymerized liposome to a specific site or cell type in order to optimize the immune response to the encapsulated antigen or the efficacy of the encapsulated therapeutic. More particularly, the present invention relates to the use of polymerized liposomes modified to contain a carbohydrate or lectin on their surface to deliver vaccines to mucosal epithelium. The present invention further relates to the synthesis, preparation and use of the modified polymerized liposomes of the present invention as, or in, pharmaceutical compositions for oral delivery of drugs and vaccines.

2. BACKGROUND OF THE INVENTION

2.1. DRUG DELIVERY

Drug delivery takes a variety of forms, depending on the agent to be delivered and the administration route. The most convenient way to administer drugs into the body is by oral administration. However, many drugs, in particular proteins and peptides, are poorly absorbed and unstable during passage through gastrointestinal (G-I) tract. The administration of these drugs is generally performed through parenteral injection.

Although oral vaccination is more convenient, vaccines are generally given through injection. This is particularly true with killed or peptidic vaccines, because of their low absorbability and instability in the G-I tract. A problem with systemic immunization is that it may not effectively induce mucosal immune responses, particularly production of IgA, that are important as the first defense barrier to invaded microorganisms. For this reason, it would be beneficial to provide oral vaccination, if the problems of low absorbability and instability could be overcome.

Controlled release systems for drug delivery are often designed to administer drugs to specific areas of the body. In the gastrointestinal tract it is important that the drug not be eliminated before it has had a chance to exert a localized effect or to pass into the bloodstream.

Enteric coated formulations have been widely used for many years to protect drugs administered orally, as well as to delay release. Several microsphere formulations have been proposed as a means for oral drug delivery. For example, PCT/US90/0643 and PCT/US90/06433 by Enzytech discloses the use of a hydrophobic protein, such as zein, to form microparticles; U.S. Pat. No. 4,976,968 to Steiner et al. discloses the use of "proteinoids" to form microparticles; and European Patent Application 0,333,523 by the UAB Research Foundation and Southern Research Institute discloses the use of synthetic polymers such as polylactic acid-glycolic acid to form in microspheres.

Particles less than ten microns in diameter, such as the microparticles of EPA 0,333,523, can be taken up by cells in specialized areas, such as Peyer's patches and other intestinal mucosal lymphoid aggregates, located in the intestine, especially in the ileum, into the lymphatic circulation. Entrapping a drug or antigen in a microparticulate system can protect the drug or antigen from acidic and enzymatic degradation, yet still allow the drug or antigen to be administered orally, where they are taken up by the specialized uptake systems, and release the entrapped material in a sustained manner or are processed by phagocytic cells such as macrophages. When the entrapped material is a drug, elimination of the first-pass effect (metabolism by the liver) is highly advantageous.

2.2. LIPOSOMES

Liposomes have been proposed for use as an oral drug delivery system, for example, by Patel and Ryman, FEBS Letters 62(1), 60–63 (1976). Liposomes are typically less than 10 microns in diameter, and, if they were stable to passage through the G-I tract, may be absorbed through Peyer's patches. Liposomes also have some features that should be advantageous for a particulate system for oral drug or antigen delivery. The phospholipid bilayer membrane of liposomes separates and protects entrapped materials in the inner aqueous core from the outside. Both water-soluble and -insoluble substances can be entrapped in different compartments, the aqueous core and bilayer membrane, respectively, of the same liposome. Chemical and physical interaction of these substances can be eliminated because the substances are in these different compartments. Further, liposomes are easy to prepare. However, liposomes are physically and chemically unstable, and rapidly leak entrapped material and degrade the vesicle structure. Without fortifying the liposomes, they are not good candidates for oral drug or antigen delivery.

Several methods have been tried to fortify liposomes. Some methods involved intercalating cholesterol into the bilayer membrane or generating the liposomes in the presence of polysaccharides. These methods are not useful in making liposome for oral delivery since during oral delivery liposomes are exposed to an acidic pH in the stomach and bile salts and phospholipases in intestine. These conditions break down the cholesterol and polysaccharide in the liposomes.

Investigators have explored the improved stability of polymerized liposomes, however in the area of drug delivery their ultimate utility remains uncertain (Regen, 1987 in Liposomes From Biophysics to Therapeutics, edit. Ostro, Marcel Dekker, N.Y.). Polymerized liposomes have been developed in attempts to improve oral delivery of encapsulated drugs (Chen et al. WO 9503035). The ability of liposomes derivatized with wheat germ agglutinin to better survive the G-I tract has also been investigated (Chen et al., 1995, Proceed. Internat. Symp. Control. Rel. Bioact. Mater. 22; Chen et al., 1995 Proc. 3rd U.S. Japan Symposium on Drug Delivery).

However, to the inventors' knowledge, to date the utility of conventional liposomes for oral delivery is still questionable. Similarly, whether polymerized liposomes are more advantageous than conventional or unpolymerized liposomes for oral drug delivery is still unclear since improved stability alone may not be sufficient for oral drug delivery, particularly oral vaccination. Thus, there remains a need for drug and antigen delivery devices that can survive the harsh conditions in the G-I tract, and effectively deliver the drug, antigen or any other therapeutic.

3. SUMMARY OF THE INVENTION

The present invention encompasses polymerized liposomes which have been modified, preferably on their surface, to contain a molecule or ligand which targets the polymerized liposome to a specific site. The invention also encompasses the use of the modified polymerized liposomes for the oral delivery of drugs and antigen delivery systems. In particular, the polymerized liposomes of the present invention are modified to contain a carbohydrate moiety or lectin which targets the liposomes to Peyer's Patch cells and mucosal epithelium.

The present invention is based on, inter alia, Applicants' discovery that the polymerized liposomes of the present invention have surprisingly enhanced stability against the harsh environment of the gastrointestinal tract particularly when compared to unpolymerized liposomes. Further, the modification of the polymerized liposomes to include lectins which have a binding affinity for the mucosal cells of the Peyer's Patch resulted in unexpectedly enhanced and rapid uptake of intact liposomes. For example, uptake or absorption into mucosal tissue is enhanced by the polymerized liposomes of the present invention whether administered orally, intranasally, sublingually, buccally or rectally. That the modified polymerized liposomes of the present invention are an optimal system for the oral and/or mucosal delivery of vaccines, allergens, drugs and therapeutics is demonstrated by the working examples described infra.

The present invention relates to the modification of the polymerized liposomes to contain molecules or ligands which target the liposomes to a specific site in order to optimize uptake of the liposome and its encapsulated therapeutic, and/or to optimize the immune response of the encapsulated antigen or the efficacy of the encapsulated drug. The polymerized liposomes of the present invention can be modified by a variety of moieties and molecules, including but not limited to, glycoproteins, carbohydrates, lectins, antibodies, antibody fragments and other molecules or proteins that may be used to target mucosal epithelium. In a preferred embodiment of the present invention, the surface of the polymerized liposomes are modified to contain carbohydrate moieties or lectins which have affinity for mucosal epithelium cells and Peyer's Patch cells. In yet another embodiment of the invention, the surfaces of the polymerized liposomes are modified to contain monoclonal antibodies which have affinity for a specific cell-surface protein. The modified polymerized liposomes are then targeted to a specific cell or organ as intact particles.

The modified polymerized liposomes of the present invention may be utilized for the delivery of a wide variety of compounds, allergens and antigens, including, but not limited to insulin peptides, diphtheria toxin antigens and influenza antigens. The modified polymerized liposomes of the present invention have particular utility in the oral and/or mucosal delivery of vaccines and antigen release devices. The modified polymerized liposomes of the present invention may also be utilized for the oral delivery of a wide variety of therapeutics, including but not limited to, chemotherapy agents for the treatment of cancer; cytokines, including interferon; and hormones including insulin, human growth hormone (HGH), fertility drugs, calcitonin, calcitriol and other bioactive steroids.

The present invention relates to the synthesis, preparation and use of the modified polymerized liposomes. The liposomes of the present invention are composed of phospholipids which are polymerized by covalent bonding to each other. Covalently bonding the layers adds strength, resulting in a less fluid unpolymerized liposome. The less fluid bi-layer membrane suppresses leakage. Further, the detergent-like bile salts in the intestine cannot solvate the phospholipid molecules. These cross-linked membranes are strong enough to maintain their structure even if the phospholipids undergo hydrolysis at low pH and enzymatic degradation by phospholipases. Thus, polymerized liposomes reach the ileum of the G-I tract as intact particulates, and are absorbed. In addition, the ligand target of the polymerized liposome must be stable to the harsh conditions of the G-I trace and the link or bond to the polymerized liposome must be sufficiently stable to remain intact until the liposome is targeted or delivered.

3.1. DEFINITIONS

As used herein, the term "liposome" is defined as an aqueous compartment enclosed by a lipid bilayer. (Stryer, *Biochemistry, 2d Edition*, W. H. Freeman & Co., p. 213 (1981)). The liposomes can be prepared by a thin film hydration technique followed by a few freeze-thaw cycles. Liposomal suspensions can also be prepared according to methods known to those skilled in the art, for example, as described in U.S. Pat. No. 4,522,811, incorporated herein by references in its entirety.

As used herein, the term "polymerized liposome" is defined as a liposome in which the constituent phospholipids are covalently bonded to each other by inter and intra molecular interactions. The phospholipids can be bound together within a single layer of the phospholipid bilayer (the leaflets) and/or bound together between the two layers of the bilayer.

The degree of crosslinking in the polymerized liposomes can range from 30 to 100 percent, i.e., up to 100 percent of the available bonds are made. The size range of polymerized liposomes is between approximately 15 nm to 10 $\mu$m. The polymerized liposomes can be loaded with up to 100% of the material to be delivered, when the material is hydrophobic and attracted by the phospholipid layers. In general, about 5 to about 40 percent of the material is encapsulated when the material is hydrophilic.

As used herein, the term "trap ratio" is defined as the ratio of inner aqueous phase volume to total aqueous phase volume used.

As used herein, the term "radical initiator" is defined as a chemical which initiates free-radical polymerization.

As used herein, the term "reverse phase evaporation technique" is defined as a method involving dissolving a lipid in an organic solvent, adding a buffer solution, and evaporating the organic solvent at reduced pressure, as described by Skoza, F. Jr., and Papahadjopoulos, D., *Proc. Natl. Acad. Sci. USA*, Volume 75, No. 9, pp. 4194–4198 (1978).

As used herein, the term "freeze-thaw technique," or "F-T," is defined as freezing a suspension in liquid nitrogen, and subsequently thawing the suspension in a roughly 30° C. water bath.

As used herein, the terms "mucosa" or "mucosal" refers to a mucous tissue such as epithelium, lamina, propria, and a layer of smooth muscle in the digestive tract. Mucosal delivery as used herein is meant to include delivery through bronchi, gingival, lingual, nasal, oral, and intestinal mucosal tissue.

As used herein, the term "buffer solution" is defined as an aqueous solution or aqueous solution containing less than 25% of a miscible organic solvent, in which a buffer has been added to control the pH of the solution. Examples of suitable buffers include but are not limited to PBS (phosphate buffered saline), TRIS (tris-(hydroxymethyl) aminomethane), HEPES (hydroxyethylpiperidine ethane sulfonic acid), and TES 2-[(tris-hydroxymethyl)methyl] amino-1-ethanesulfonic acid.

As used herein, the term "leaflets" is defined as a single layer of phospholipid in the bilayer forming the liposome.

4. BRIEF DESCRIPTION OF THE DRAWINGS

FIG. 1 is a graph of the percent BSA (Bovine Serum Albumin) released from polymerized liposomes of DODPC (1,2-di(2,4-Octadecadienoyl)-3-phosphatidylcholine), in various solvent systems, as a function of time (in days). The open circles represent release of BSA in a solution buffered to pH 7 with Tris-saline. The darkened triangles represent the release of BSA in a solution of pH 2 saline. The darkened squares represent the release of BSA in a solution of bile (PLA and TCA).

FIG. 2 is a graph of the percent BSA (Bovine Serum Albumin) released from unpolymerized liposomes of DOPC (1,2-di(2,4-Octadecadienoyl)-3-phosphatidylcholine), in various solvent systems, as a function of time (in days). The open circles represent the release of BSA in a solution buffered to pH 7 with Tris-saline. The darkened triangles represent the release of BSA in a solution of pH 2 saline. The darkened squares represent the release of BSA in a solution of bile (PLA and TCA).

FIG. 3 is a graph of the percent BSA (Bovine Serum Albumin) released from liposomes of hydrogenated egg phosphatidylcholine and cholesterol, in various solvent systems, as a function of time (in days). The open circles represent release of BSA in a solution buffered to pH 7 with Tri-saline. The darkened triangles represent the release of BSA in a solution of pH 2 saline. The darkened squares represent the release of BSA in a solution of bile (PLA and TCA).

FIG. 4 is a graph of the total absorption of radioactive protein (in picocuries) as a function of time (in hours). The darkened bars represent the absorption of protein from polymerized liposomes. The hashed bars represent the absorption of protein from unpolymerized liposomes. The white bars represent the absorption of protein from a protein solution.

Figure 7:
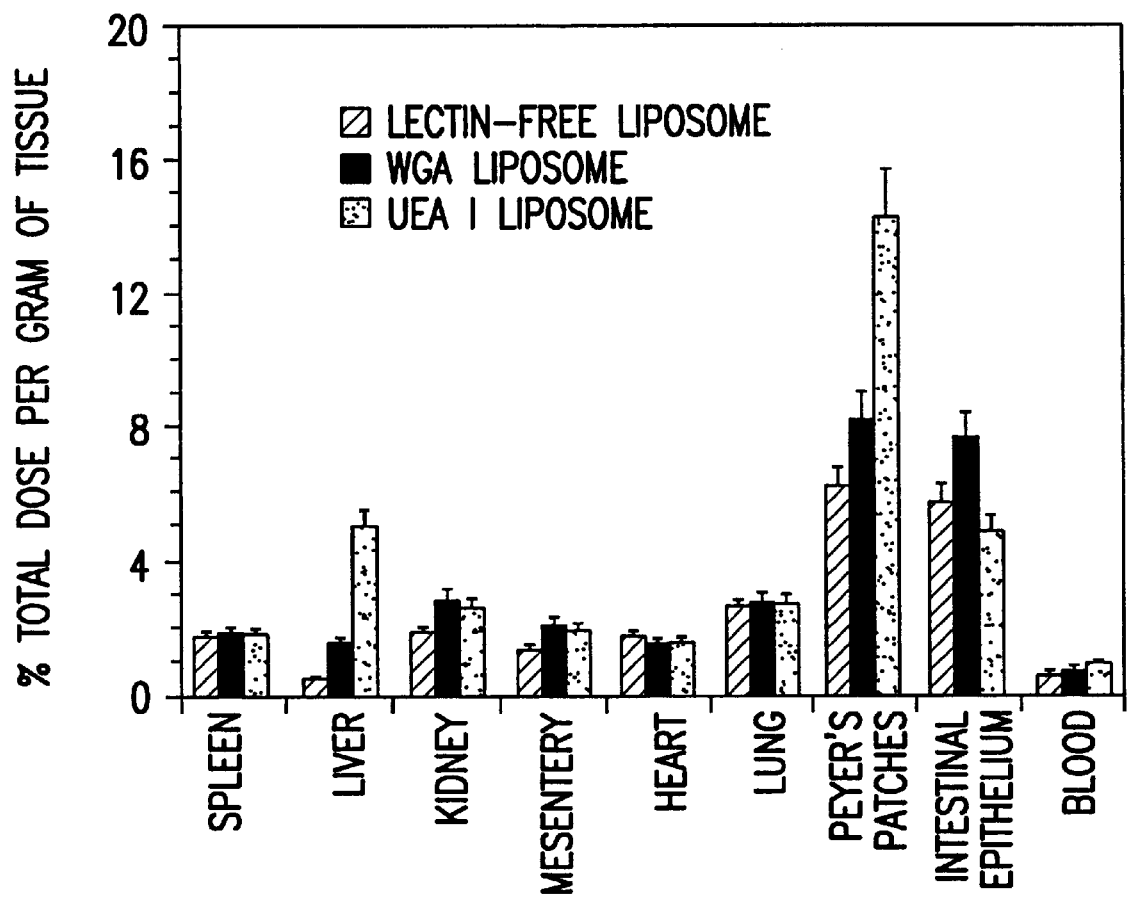

FIG. 7 shows the in vivo distribution of lectin-free liposomes, WGA liposomes, and UEA liposomes in mouse tissues after a single dose oral administration. Each column represents the average of data collected from four mice. The errors presented were standard deviations.

Figure 8:
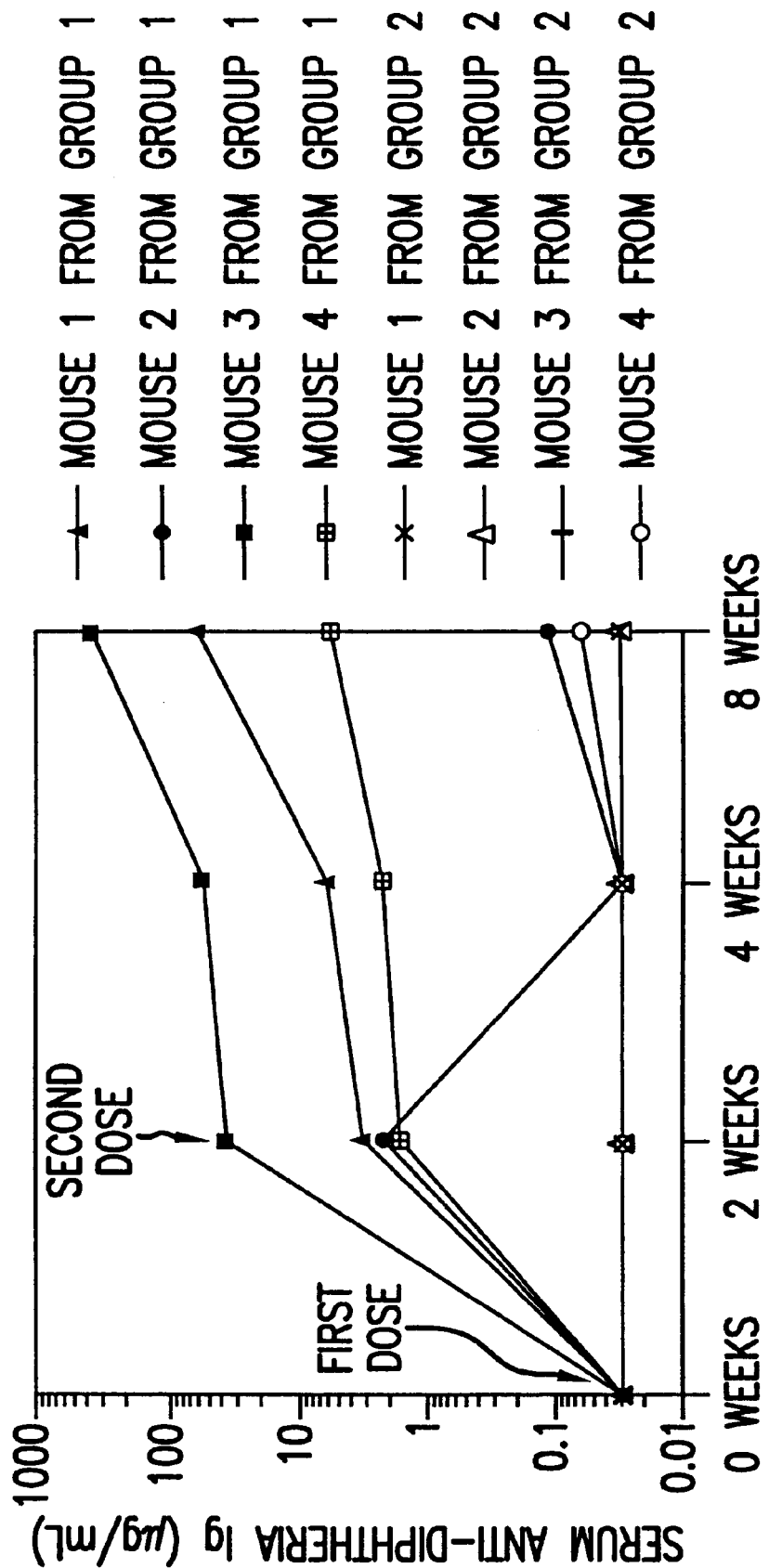

FIG. 8 shows serum Ig levels in mice who were administered with diphtheria toxoid-containing polymerized liposomes of polymerized liposomes mixed with diphtheria toxoid.

Figure 9:
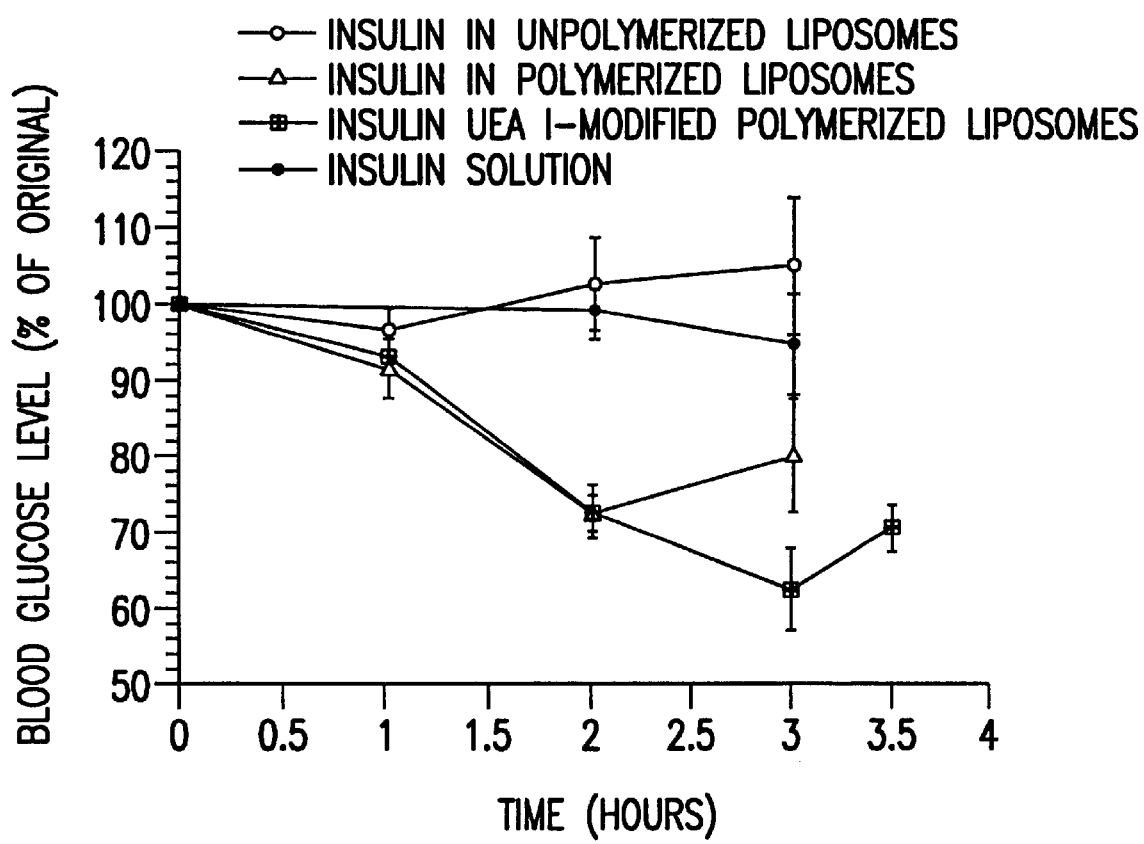

FIG. 9 shows blood glucose level after a single dose oral administration of different preparations. Each data point is the average of three mice, and the error bars presented are standard errors.

5. DETAILED DESCRIPTION OF THE INVENTION

The present invention relates to targeted polymerized liposomes for oral and/or mucosal delivery of vaccines, allergens and therapeutics. In particular, the present invention relates to polymerized liposomes which have been modified, particularly on their surface to contain a molecule or moiety which target the polymerized liposome to a specific site or cell type in order to optimize uptake and the immune response to the encapsulated antigen or the efficacy of the encapsulated drug. In one embodiment of the present invention, the polymerized liposomes are modified with lectins and targeted to mucosal epithelium of the small intestine and are absorbed into the systemic circulation and lymphatic circulation.

The present invention is based in part on Applicants' discovery that the polymerized liposomes of the present invention have surprisingly enhanced stability against the harsh environment of the gastrointestinal tract. Further, the modification of the polymerized liposomes to include lectins which have a particularly affinity for the mucosal cells of Peyer's patches resulted in unexpectedly enhanced and rapid uptake of intact liposomes. That the modified polymerized liposomes of the present invention are an optimal system for the oral and/or mucosal delivery of vaccines, allergens, drugs and therapeutics is demonstrated by the working examples described infra. Particularly surprising, and especially beneficial, is the utility of the targeted polymerized liposomes for oral vaccination.

The present invention relates to polymerized liposomes which have been modified to contain a molecule or a moiety which targets the polymerized liposome. The polymerized liposomes of the present invention may be modified to include a variety of molecules and moieties to target the liposomes, including but not limited to glycoproteins, peptides, carbohydrates, lectins i.e., ulex europeas agglutinin I, monoclonal antibodies, cholera toxin B subunit, bacterial adhesotopes or phage display hybrid peptides encompassing binding domains and magnetic particles. In a preferred embodiment of the invention, the polymerized liposomes are modified to contain a carbohydrate moiety or lectin which targets the liposome to small intestine Peyer's Patch cells and mucosal epithelium. In particular, the polymerized liposomes of the present invention are modified with carbohydrate moieties or lectins which specifically recognize sugar moieties selectively expressed on the cell surface of M cells and Peyer's patch cells; for example, fucosyl sugars. These molecules and moieties may be attached to the surface of the liposomes by a variety of methods, for example, by derivatizing the carbohydrate or lectin moiety with a hydrophobic anchor, N-glutaryl-phosphatidylethanolamine (NGPE), see e.g., Chen et al., 1995, Proceed. Internat. Symp. Control. Rel. Bioact. Mater. 22.

The modified polymerized liposomes of the present invention have utility for the oral and/or mucosal delivery of antigens, allergens, vaccines and therapeutics. The modified polymerized liposomes of the present invention are designed to deliver a wide variety of therapeutics including RNA and DNA nucleotides as used, for example, in gene therapy, peptides and small molecules. These therapeutics include but are not limited to antiviral agents, antibacterial agents, attenuated viruses, antifungal agents, cytokines, hormones, insulin, calcitonin, fertility drugs, antibiotics and chemotherapy agents.

The present invention also relates to the synthesis, preparation and the use of the modified polymerized liposome. The liposomes of the present invention are generally prepared by polymerization of double and triple bond-containing monomeric phospholipids. In a preferred embodiment, examples of polymerizable functional groups, include but are not limited to olefins, acetylenes, and thiols. The liposomes of the present invention may be polymerized by a variety of techniques including but not limited to free radical initiation and radiation. The polymerized liposomes of the present invention may be prepared by a variety of techniques as described intra.

5.1. TARGETING MOLECULES

A variety of molecules and ligands may be used to modify the polymerized liposomes of the present invention in order to target them to a specific site cell type, including, but not limited to, glycoproteins, carbohydrates, lectins, monoclonal antibodies, antibody fragments, viral proteins, bacterial proteins, i.e., cholera toxin B subunit, phage display hybrid peptides and magnet tic particles.

In a preferred embodiment of the present invention carbohydrates or lectins are used to target the polymerized liposomes of the present invention to M cells and Peyer's Patch cells of the small intestine. In another preferred embodiment of the present invention, lectins which bind to fucosyl sugars are used to modify the polymerized liposomes. Lectins are a heterogenous group of proteins or glycoproteins that recognize carbohydrate residues on cell surface glycoconjugates with a high degree of specificity. Examples of lectins that may be used to modify the polymerized liposomes of the present invention, include but are not limited to, lectins specific for fucosyl glycoconjugates, such as Ulex Europeas Agglutinin I (UEA); lectins specific for galactose/N-acetylgalactoseamine, such as Phaseolus vulgaris haemagglutinin (PHA), tomato lectin (Lycopersicon esculentum) (TL), wheat germ agglutinin (WGA); lectins specific for mannose, such as, Galanthus nivalis agglutinin (GNA); lectins specific for mannose/glucose, such as, con A/concavalan A. (See e.g., Lehr et al., 1995, in Lectins Biomedical Perspectives, pp. 117–140). These targeting molecules can be derivatized if desired. See e.g., Chen et al., 1995, Proceed. Internat. Symp. Control. Rel. Bioact. Mater. 22 and Cohen WO 9503035.

In another embodiment of the invention, polymerized liposomes may be modified with viral proteins or bacterial proteins that have an affinity for a particular residue expressed on a cell surface or that have an affinity for a cell surface protein or receptor. Examples of such proteins include, but are not limited to, cholera toxin B subunit, bacterial adhesotopes.

In yet another embodiment of the present invention, polymerized liposomes may be modified with monoclonal antibodies or fragments of antibodies which target the polymerized liposome to a particular cell type. The polymerized liposomes of the present invention may be modified with ligands for specific mucosal cell surface receptors and proteins. As used herein, the term "ligand" refers to a ligand attached to the polymerized liposomes which adheres to the mucosa in the intestine or can be used to target the liposomes to a specific cell type in the G-I tract or following absorption. These can range from ligands for specific cell surface proteins and antibodies or antibody fragments immunoreactive with specific surface molecules, to less specific targeting such as coatings of materials which are bioadhesive, such as alginate and polyacrylate. In general, ligands are bound to or inserted within the polymerized phospholipids; adhesive polymers are applied as a coating to the particles.

As noted above, the liposomes can be modified, for example, by attaching to the surface of the particle specific ligands for given cells in a mixture of cells. When magnetic particles are also incorporated, the particles can be targeted using the ligands, such as tissue specific surface proteins, then maintained as the targeted cells using a magnetic field while the particles are imaged or a compound to be delivered is released. Such magnetic particles are known in the art and include aqueous-based ferro fluid EMB 807 (Ferrofluids, NH).

5.2. MATERIALS TO BE ENCAPSULATED

The modified polymerized liposomes of the present invention have utility for the oral and/or mucosal delivery of vaccines, antigens, allergens, therapeutic agents and drugs. The polymerized liposomes of the present invention may be designed to carry a wide variety of antigens including, but not limited to diphtheria toxoid, influenza hemeagglutinin, ospA antigen from Lyme disease bacterium, and HTLV envelope protein antigen. Antigens to poliovirus, rhinovirus, rabies, vaccinia, Epstein-Barr virus, hepatitis, HTLV, herpes virus and human immunodeficiency virus are just examples of the many types of antigens which may be encapsulated into the liposomes of the present invention.

The modified polymerized liposomes of the present invention can be used for the oral and/or mucosal delivery of a wide variety of therapeutics, including but limited to, chemotherapy agents, antibiotics, insulin, cytokines, interferon, hormones, calcitonin, hormones, fertility drugs, antiviral agents (ddI, AZT, ddC, acyclovir and the like), antibacterial agents, antifungal agents, DNA and RNA nucleotides, i.e., useful for gene therapy.

As used herein, the term "biologically active substance" refers to eukaryotic and procaryotic cells, viruses, vectors, proteins, peptides, nucleic acids, polysaccharides and carbohydrates, lipids, glycoproteins, and combinations thereof, and synthetic organic and inorganic drugs exerting a biological effect when administered to an animal. For ease of reference, the term is also used to include detectable compounds such as radiopaque compounds including air and barium, magnetic compounds, fluorescent compounds, and radioactive compounds. The active substance can be soluble or insoluble water. Examples of biologically active substances include anti-angiogenesis factors, antibodies, antigens, growth factors, hormones, enzymes, and drugs such as steroids, anti-cancer drugs or antibiotics, as well as materials for use as insecticides or insect repellents, fertilizers and vitamins, or any other material having a biological effect where controlled release is desirable.

In a diagnostic embodiment, the polymerized liposome incorporates a pharmaceutically acceptable gamma-emitting moiety, including but not limited to, indium and technetium, magnetic particles, radiopaque materials such as air or barium and fluorescent compounds.

5.3. PREPARATION OF POLYMERIZED PHOSPHOLIPIDS

The polymerized liposomes of the present invention may be prepared by a variety of techniques as described infra. For example, and not by way of limitation, polymerized liposomes are prepared by polymerizing double and triple bond-containing olefinic and acetylenic phospholipids. In addition, polymerized liposomes can be prepared by chemical oxidation of thiol groups in the phospholipids to disulfide linkages. The polymerization can take place in a solution containing a biologically active substance, such as a drug or antigen, in which case the substance is encapsulated during the polymerization. Alternatively, the liposomes can be polymerized first, and the biologically active substance can be added later by resuspending the polymerized liposomes in a solution of a biologically active substance, and entrapping the substance by sonification of the suspension. Another method of entrapping a biologically active substance in polymerized liposomes is to dry the polymerized liposomes to form a film, and hydrate the film in a solution of the biologically active substance. The above conditions are typically mild enough to entrap biologically active substances without denaturing them.

The polymerized liposomes are generally prepared by polymerization of double bond-containing monomeric phospholipids. These phospholipids may contain any unsaturated functional group, including polymerizable functional group double or triple bonds, any may contain more than one polymerizable functional group double or triple bonded. Suitable monomeric phospholipids are known to those skilled in the art, and include, but are not limited to, phosphatidylcholines DODPC (1,2-di(2,4-Octadecadienoyl)-3-phosphatidylcholine), 2,4-diene phospholipids, diyne phospholipids, see e.g., U.S. Pat. No. 4,485,045, U.S. Pat. No. 4,861,521. If the liposome is polymerized by oxidation of thiol groups, it is preferred not to encapsulate thiol-containing biologically active substances, as they could be oxidized during the polymerization step.

The liposomes of the present invention may be polymerized by free radical initiation. The monomeric double bond-containing phospholipids can be polymerized using a hydrophobic free radical initiator, such as AIBN (azo-bis-isobutyronitrile), or a hydrophilic free radical initiator such as AAPD (azo-bis-amidinopropane dihydrochloride). The latter is particularly useful for initiating polymerization between layers of the bilayer. The present invention also encompasses the use of other mild redox initiators, such as $Na_2S_2O_5$ and $K_2S_2O_8$. Alternatively, polymerization can be initiated by using a radiation source, such as ultraviolet or gamma radiation. Use of the free radical initiators is preferred if the biologically active substance to be entrapped is denatured when exposed to radiation.

The ratio between the phospholipid and crosslinker and aqueous phase all affect the percent of crosslinking. In general, the percent crosslinking increases as the amount of crosslinker or time or temperature of reaction are increased. As the percent crosslinking increases, the release rate of the materials from the liposomes decreases and the stability increases.

The liposomes of the present invention may be polymerized by radiation including, polymerization with ultraviolet and/or gamma radiation, provided the biologically active substance can survive exposure to the radiation. Typical conditions for initiating the polymerization with ultraviolet radiation include but are not limited to irradiating the solution at 254 nm, 100 W, for 3 hours at room temperature. Typical conditions for initiating the polymerization with gamma radiation include but are not limited to irradiating the solution at 0.3 mRad per hour for 3 hours at room temperature.

5.4. ENCAPSULATION OF BIOLOGICALLY ACTIVE MATERIAL

Materials are generally incorporated into the liposomes at the time of formation, following polymerization using sonication of a solution of the material which contains the liposomes, and following polymerization by rehydration of a thin film of the liposomes.

The following is a general method for the preparation of polymerized liposomes wherein a biologically active substance is entrapped prior to the polymerization of the monomeric double bond-containing liposome. First, the monomeric liposome is prepared by the thin film hydration of a monomeric double bond-containing phospholipid. The monomeric phospholipid is dissolved, and the solution is then dried to form a thin film of phospholipid. A solution containing substance to be entrapped is added, preferably with a catalytic amount (1–3 percent by weight) of free radical initiator. At this stage, it is preferable to establish an inert atmosphere. The lipid film is then hydrated by gently shaking and sonicating the solution at a temperature of from 30 to 50° C., usually around 40° C., for between five minutes and two hours, preferably around five minutes. Once the lipid film is hydrated, the trap ratio of the liposome can be increased by performing one or more freeze-thaw cycles on the liposome solution. This is particularly useful when the material being incorporated is hydrophilic in nature. Next, the polymerization is carried out at an elevated temperature, from 60 to 100° C., preferably at around 60° C., for 5 to 20 hours, preferably about 5 hours, or until the polymerization is essentially complete. The desired degree of crosslinking is from 30 to 100 percent.

Unentrapped biologically active substance can be removed by several means, including repeated centrifugation, decantation, gel filtration, and dialysis. The polymerized liposomes are then suspended in a buffer solution. The buffer solution has a pH preferably between pH 4.5 and pH 9.5, more preferably at physiological pH.

This method of entrapping biologically active substances is preferred because it does not involve the use of organic solvents. Use of organic solvents can denature biologically active substances. Further, the temperature requirements are mild, with the temperature typically not exceeding 60° C.

If the biologically active substance cannot tolerate the temperature conditions or exposure to radiation, a third member of entrapping the substance in a polymerized liposome is preferred. In this method, the liposomes are polymerized before adding the material to be encapsulated. After the polymerization is complete, the polymerized liposomes are added to an aqueous solution of the material. The solution should be aqueous, although it can include small amounts of organic solvent. The solution is sonicated, and the sonication entraps the substance inside the polymerized liposome.

Another method for entrapping biologically active substances in polymerized liposomes is to dissolve the partially polymerized liposomes in a suitable organic solvent, such as tetrahydrofuran, acetone, ether, chloroform, methylene dichloride, and ethyl acetate, and evaporate the solvent to form a thin film of partially polymerized liposome. Following encapsulation, polymerization is completed. Hydrophobic materials are preferably encapsulated in the liposomes by dissolving the materials in an organic solvent with the phospholipid, before forming the liposomes. Hydrophilic materials are more preferably incorporated by hydrating a thin film of polymerized liposomes in the presence of an aqueous solution of the substance.

Materials can be entrapped within the liposomes, as well as or alternatively in one or more of the lipid layers of the phospholipid bilayer. This is typically determined by the hydrophobicity/hydrophilicity of the material to be incorporated as well as the method of preparation.

5.5. MODES OF ADMINISTERING THE POLYMERIZED LIPOSOMES TO A PATIENT

The polymerized liposomes of the present invention are administered by those routes which optimize uptake by mucosa. For example, oral, sublingual, buccal, rectal and intranasal are preferred routes of administration. However, topical, transdermal and parenteral delivery may also be used. The most preferred route is oral. Further, the polymerized liposomes are particularly suitable for delivery through mucosal tissue or epithelia. The polymerized liposomes of the invention can be delivered orally in the form of tablets, capsules, cachets, gelcaps, solutions, suspensions and the like. When the dosage unit form is a capsule, it can contain, in addition to the material of the above type, a liquid carrier or adjuvant, when the liposomes contain an antigen. If administered topically the liposomes will typically be administered in the form of an ointment or transdermal patch. If administered intranasally the liposomes will typically be administered in an aerosol form, or in the form of drops. Suitable formulations can be found in Remington's Pharmaceutical Sciences, 16th and 18th Eds., Mack Publishing, Easton, Pa. (1980 and 1990), and Introduction to Pharmaceutical Dosage Forms, 4th Edition, Lea & Febiger, Philadelphia (1985), each of which is incorporated herein by reference.

The polymerized liposomes of the present invention are suitable for administration to mammals, including humans, as well as other animals and birds. For example, domestic animals such as dogs and cats, as well as domesticated herds, cattle, sheep, pigs and the like may be treated or vaccinated with the polymerized liposomes of the present invention.

The modified polymerized liposomes of the present invention have use in vaccine preparations. The preparation of vaccines containing an immunogenic polypeptide as the active ingredient is known to one of skill in the art.

5.5.1. DETERMINATION OF VACCINE EFFICACY

The immunopotency of the oral vaccines of the present invention can be determined by monitoring the immune response in test animals following immunization with the vaccine of choice, or by use of any immunoassay known in the art. Generation of a humoral response, mucosal response and/or cell-mediated immunity, may be taken as an indication of an immune response. Test or treatment animals may include mice, hamsters, dogs, cats, monkeys, rabbits, chimpanzees, and human subjects.

Methods of introducing the vaccine are preferably oral, although they may also include intracerebral, intradermal, intramuscular, intraperitoneal, intravenous, subcutaneous, intranasal or any other standard routes of immunization. The immune response of the test subjects can be analyzed by various approaches such as: the reactivity of the resultant immune serum to the antigen of choice, as assayed by known techniques, e.g., immunosorbant assay (ELISA), immunoblots, radioimmunoprecipitations, etc., or in the case where the antigen displays antigenicity or immunogenicity, by protection of the immunized host from the virus and/or attenuation of symptoms due to infection by the virus in the immunized host.

As one example of suitable animal testing of a vaccine, the vaccine of the invention may be tested in rabbits for the ability to induce an antibody response to the antigen. Male specific-pathogen-free (SPF) young adult New Zealand White rabbits may be used. The test group each receives a fixed concentration of the vaccine. A control group receives a dose of liposomes without the antigen. Blood samples may be drawn from the rabbits every one or two weeks, and serum analyzed for antibodies to the protein. The presence of antibodies specific for the antigen may be assayed, e.g., using an ELISA.

5.5.2. VACCINE FORMULATIONS

Suitable preparations of such vaccines include injectables, either as liquid solutions or suspensions; solid forms suitable for solution in, suspension in, liquid prior to injection, may also be prepared. The active immunogenic ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

Examples of adjuvants which may be effective, include, but are not limited to: aluminum hydroxide, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine.

The effectiveness of an adjuvant may be determined by measuring the induction of antibodies directed against an immunogenic polypeptide containing an antigenic epitope, the antibodies resulting from administration of this polypeptide in vaccines which are also comprised of the various adjuvants.

The polypeptides may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The vaccines of the invention may be multivalent or univalent. Multivalent vaccines are made from recombinant viruses that direct the expression of more than one antigen.

Many methods may be used to introduce the vaccine formulations of the invention; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats.

The vaccine formulations of the invention comprise an effective immunizing amount of the antigenic protein and a pharmaceutically acceptable carrier or excipient. Vaccine preparations comprise an effective immunizing amount of one or more antigens and a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided so that the ingredients may be mixed prior to administration.

The precise dose of vaccine preparation to be employed in the formulation will also depend on the route of administration, and the nature of the patient, and should be decided according to the judgment of the practitioner and each patient's circumstances according to standard clinical techniques. An effective immunizing amount is that amount sufficient to produce an immune response to the antigen in the host to which the vaccine preparation is administered.

Use of purified antigens as vaccine preparations can be carried out by standard methods. For example, the purified protein(s) should be adjusted to an appropriate concentration, formulated with any suitable vaccine adjuvant and encapsulated within the polymerized liposome. Suitable adjuvants may include, but are not limited to: mineral gels, e.g., aluminum hydroxide; surface active substances such as lysolecithin, PLURONIC polyols; polyanions; peptides; oil emulsions; alum, and MDP. The immunogen may also be incorporated into liposomes, or conjugated to polysaccharides and/or other polymers for use in a vaccine formulation. In instances where the recombinant antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

Effective doses (immunizing amounts) of the vaccines of the invention may also be extrapolated from dose-response curves derived from animal model test systems.

The present invention thus provides a method of immunizing an animal, or treating or preventing various diseases or disorders in an animal, comprising administering to the animal an effective immunizing dose of a vaccine encapsulated within a targeted polymerized liposomes of the present invention.

5.5.3. USE OF ANTIBODIES GENERATED BY THE VACCINES OF THE INVENTION

The antibodies generated against the antigen by immunization with the polymerized liposome delivered antigenic protein also have potential uses in diagnostic immunoassays, passive immunotherapy, and generation of antiidiotypic antibodies.

The generated antibodies may be isolated by standard techniques known in the art (e.g., immunoaffinity chromatography, centrifugation, precipitation, etc.) and used in diagnostic immunoassays. The antibodies may also be used to monitor treatment and/or disease progression. Any immunoassay system known in the art, such as those listed supra, may be used for this purpose including but not limited to competitive and noncompetitive assay systems using techniques such as radioimmunoassays, ELISA (enzyme-linked immunosorbent assays), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, to name but a few.

The polymerized liposome encapsulated vaccines of the present invention can also be used to produce antibodies for use in passive immunotherapy, in which short-term protection of a host is achieved by the administration of pre-formed antibody directed against a heterologous organism.

The antibodies generated by the vaccines of the present invention can also be used in the production of antiidiotypic antibody. The antiidiotypic antibody can then in turn be used for immunization, in order to produce a subpopulation of antibodies that bind the initial antigen of the pathogenic microorganism (Jerne, 1974, Ann. Immunol. (Paris) 125c:373; Jerne et al., 1982, EMBO J. 1:234).

In immunization procedures, the amount of immunogen to be used and the immunization schedule will be determined by a physician skilled in the art and will be administered by reference to the immune response and antibody titers of the subject.

5.5.4. PACKAGING

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

The present invention will be further understood by reference to the following non-limiting examples.

6. EXAMPLE 1: PREPARATION OF POLYMERIZED LIPOSOMES

In a typical preparation, 80 mg of the polymerizable phospholipid, 1,2-di(2,4-Octadecadienoyl)-3-phosphatidylcholine (DODPC), 1.68 mg of Azo-bis-isobutyronitrile (AIBN) as a radical initiator, and lipid A derivative as an adjuvant were dissolved in 4 mL chloroform. The solution was dried in vacuo to form a thin film on the inside wall of a round bottom flask. A vaccine solution (1 mL of a 1 mg/mL solution) containing 2.68 mg of Azo-bis-(amidinopropane)dihydrochloride (AAPD) as another radical initiator was added to the flask. A nitrogen atmosphere was established and the flask was sealed. The lipid film was gradually hydrated by gently shaking the flask at 40° C. for 5 minutes, followed by tip-sonication (10 W for 10 seconds). To increase the trap ratio, the liposome suspension was subjected to three freeze-thaw cycles, by freezing the suspension in liquid nitrogen and then thawing the suspension in a 30° C. water bath. The liposome suspension was polymerized at 60° C. for 5 hours, at which time polymerization was completed. Polymerization was considered complete when 95% of the double or triple bonds are crosslinked. Unentrapped vaccine antigen was removed by repeated centrifugation cycles and addition of fresh buffer. Finally, the polymerized liposomes were suspended in the appropriate buffer solution.

The liposomes were in the size range of 4±2 $\mu$m diameter as measured by a Coulter Counter particle sizer. The trap ratio of vaccine solution in polymerized liposomes (35%) was similar to that of pre-polymerized liposome preparations. The trap ratio of 35% is comparable to that of liposomes prepared by other techniques such as the "reverse phase evaporation technique". Further, the water insoluble adjuvant was embedded in the liposome membrane practically without any loss during the preparation process.

The inside structure of each liposome was drastically changed following the freeze-thaw (F-T) treatment, as determined by freeze-fracture electron microscopy. Originally, the liposomes had multi-layered structures and a small volume of inside aqueous phase. The freeze-thaw treatment reduced the number of layers and increased the volume of inner aqueous phase. Additionally, freeze-thaw treatment equilibrated the concentration of solute in the aqueous phase inside and outside of the liposomes. As a result, the trap ratio increased from a few % to around 35%.

The concentration of entrapped material in the final liposome suspension can be controlled by the original concentration of the material to be entrapped in the aqueous phase used for preparation, and the volume of continuous aqueous phase in which liposomes are suspended.

7. EXAMPLE 2: IN VITRO RELEASE OF ENTRAPPED MATERIAL $^{14}$C labelled bovine serum albumin (BSA) was used as a model protein to follow the in vitro release profiles of the material incorporated in liposomes. The polymerized liposomes containing $^{14}$C labelled BSA were prepared as described in Example 1. Additionally, non-polymerized liposomes of the same phospholipid composition (DODPC) and of hydrogenated egg phosphatidylcholine and cholesterol (molar ratio 1:1) were prepared as controls by the same procedure but were not polymerized. The particle sizes and trap ratios of the reference samples were similar to those of the polymerized liposomes.

Release studies were conducted in 1) pH 7.4 isotonic Tris buffered saline, 2) pH 2.0 isotonic HCl saline, and 3) pH 7.4 isotonic Tris saline containing 20 nM sodium taurocholate, 5 U/mL phospholipase $A_2$, and 2 nM $CaCl_2$. The latter two media simulate physiological conditions in the stomach and the intestine fluid, respectively.

Figure 1:
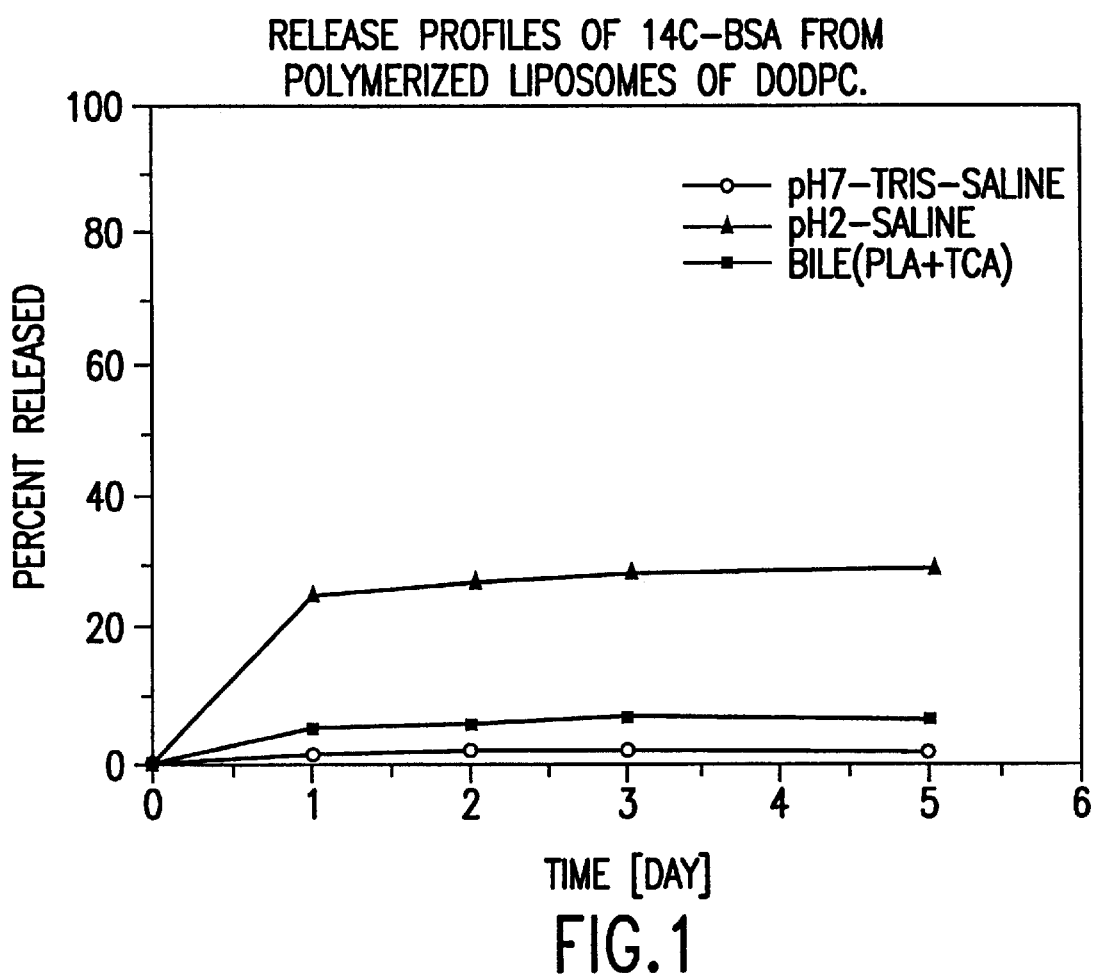
Figure 2:
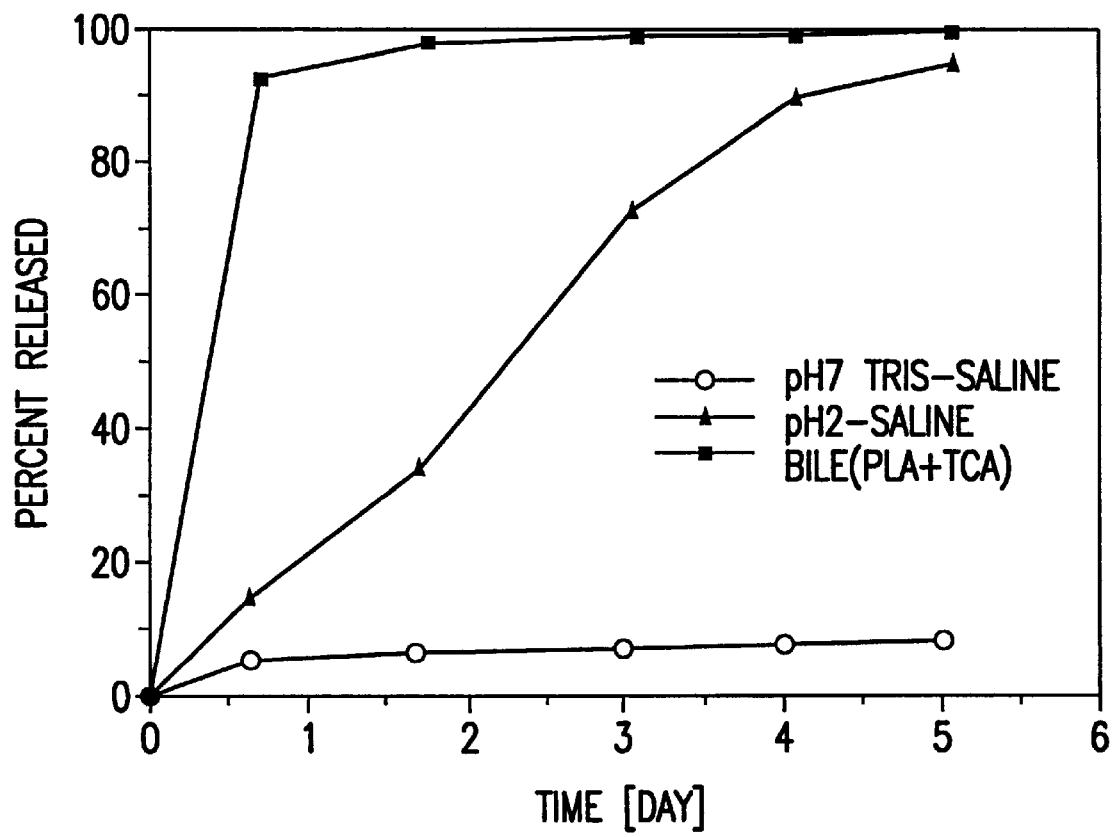
Figure 3:
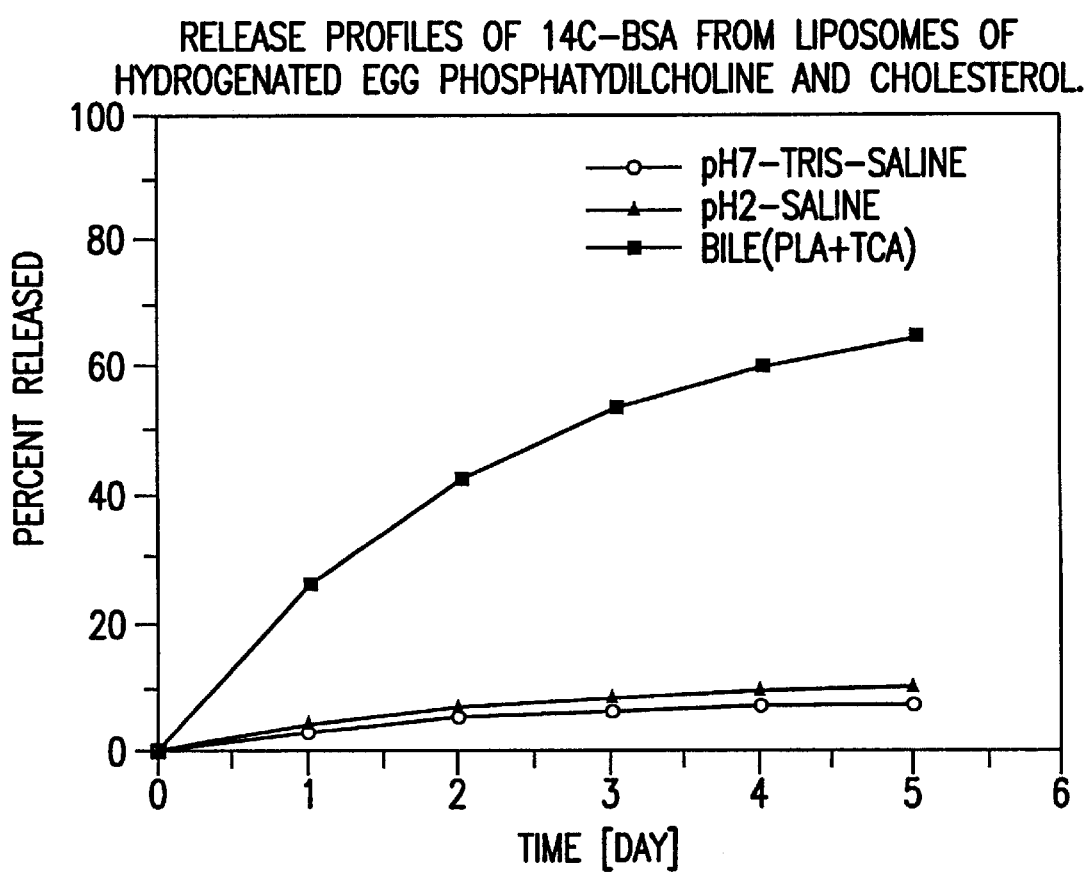

The results of release studies are shown in FIGS. 1, 2 and 3. FIG. 1 displays slow release rates of protein from polymerized liposomes. In acidic solution, less than 5% was released after 6 hours incubation in acidic medium. This would generally be the longest retention time of the liposomes in the stomach, and indicates the polymerized liposomes are stable to acid pH during transit through the stomach. In intestinal-simulated media, there was less than 5% release even after 5 days. These conditions, in general, destabilize liposomes. FIG. 2 shows faster release rates from non-polymerized liposomes, of about 90% after 1 day in the intestinal-simulated medium.

The bi-layers in the polymerized liposomes are stabilized by polymerizing the phospholipids. This stabilization is likely the cause of the slower release in the polymerized liposomes relative to the unpolymerized liposomes. FIG. 3 shows protein release patterns from hydrogenated egg phosphatidyl choline (PC) liposomes containing cholesterol. Although this liposome preparation is considered the most stable among conventional liposomes, it shows faster release rates in the intestinal-simulated media (about 30% after 5 days) than polymerized liposomes.

8. EXAMPLE 3: MEASUREMENT OF THE ABSORPTION OF BIOLOGICALLY ACTIVE SUBSTANCES ENTRAPPED IN POLYMERIZED LIPOSOMES

Polymerized liposomes containing $^{125}$I-BSA were orally administered to rats. The absorption of $^{125}$I-BSA into the blood was then examined. $^{125}$I-BSA containing monomeric liposomes and $^{125}$I-BSA solution were used as controls. The polymerized liposomes were prepared as described in Example 1. Monomeric liposomes were made of hydrogenated egg phosphatidylcholine and cholesterol (1:1 molar ratio).

Figure 4:
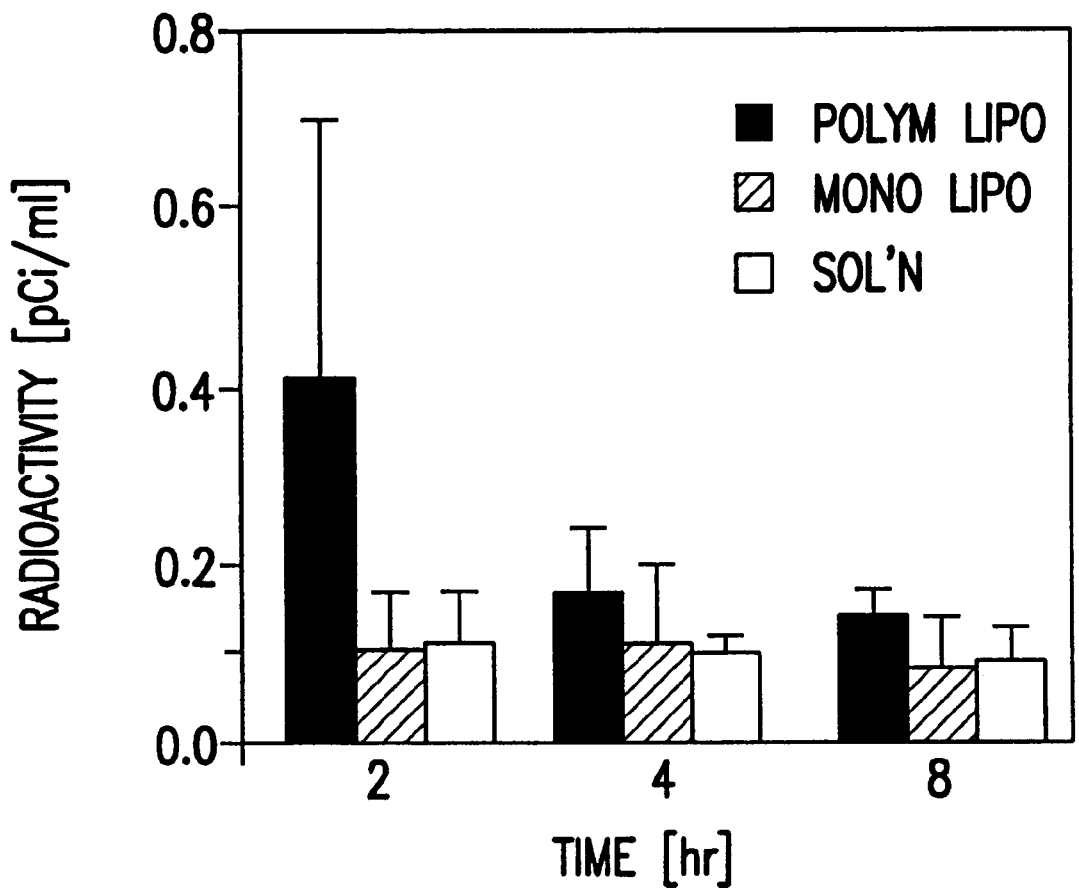

Each formulation, including the control $^{12}$I-BSA solution, was administered intragastrically with ball-tipped needle and blood was sampled at appropriate intervals from the tail vein. To distinguish between transport of $^{125}$I-BSA in the context of liposomes, free $^{125}$I-BSA and the radiolabelled degradation product of $^{125}$I-BSA, the blood samples were separated into three fractions: 1) cell debris fraction, 2) trichloroacetic acid (TCA) precipitable fraction, and 3) TCA non-precipitable fraction. FIG. 4 shows the sum of the radioactivities belonging to the fractions 1) and 2) in the blood of rats to which each dosage form was administered orally.

The results show that the "effective uptake" is much more from polymerized liposomes administration. Feces of rats were homogenated with water and centrifuged to separate solid stuff. Radioactivity in the whole homogenate and sedimented solid were compared. In the case of polymerized liposome administered rats, almost 80% of total radioactivity was observed in the solid, compared with only 10% from monomeric liposome administered rats. This result suggest that polymerized liposomes are so stable in the G-I tract that the liposomes of this formulation remain as intact structures until excreted.

Because elimination of the precipitable fraction in blood after intravenous injection was slow, i.e., 75% remaining at 6 hours after injection, the TCA non-precipitable fraction was smaller in animals administered material in polymerized liposomes, as compared to material administered in conventional liposomes and significantly less than when material was administered in solution.

9. EXAMPLE 4: LECTIN MODIFICATION OF POLYMERIZED LIPOSOMES

In these studies, polymerized liposomes surfaces were modified with lectin molecules, UEAI and WGA, in attempts to improve liposome delivery efficiency. WGA fails to specifically bind to M cells since it has affinity for sialic acids and binds to all epithelial cells with equal specificity.

9.1. MATERIALS AND METHODS

Lectin Modification

UEA I and WGA (both purchased from Sigma, St. Louis, Mo.) were derivatized with N-glutaryl-phosphatidylethanolamine (NGPE, Avanti Polar Lipids, Inc., Alabaster, Ala.) using 1-ethyl-3-(3'-dimethylaminopropyl) carbodiimide (EDC, Pierce, Rockford, Ill.) and N-hydroxysulfosuccinimide (NHS, Pierce) (Weissig et al 1986 FEBS Letters 202:86–90). Briefly, 1.2 mg of dried NGPE was dissolved in 2 mL MES buffer (50 mM, pH 5.5) containing 5 mg/mL n-octylglucoside (Sigma). 48 mg EDC and 60 mg NHS were then added and the mixture incubated at room temperature for 5 minutes before 4 mL of HEPES buffer (pH 7.5) containing 2 mg/mL UEA I or WGA was added. The pH of the reaction mixture was adjusted to 7.6 and the mixture was incubated overnight at 4° C. under constant gentle agitation. The product was dialyzed in a Spectrum™ dialysis tube (MWCO 1,000) overnight against PBS (20 mM, pH7.6) in the presence of 50 mg Biobeads™ (Biorad, Hercules, Calif.) to facilitate the removal of detergent and other excess reagents. The final solution was stored at 4° C. until use.

Determination of the Degree of Lectin Modification

The degree of modification was determined with the 2,4,6-trinitro-benzenesulphonic acid (TNBS, Sigma) assay. 700 µL of 0.1 M sodium borate buffer (pH 9.2). 350 µL of TNBS aqueous solution (1.65 mg/mL) was added and the solution was rapidly mixed. After incubation at 40° C. for 45 minutes, the reaction was stopped by adding 350 µL of 0.1 M $NaH_2PO_3$ and absorbance at 420 nm was determined on a UV/VIS spectrometer (Perkin-Elmer 553, Newton Center, Mass.).

Formation of Lectin-bearing Polymerized Liposomes 30 mg of DODPC was dissolved in chloroform and ethyl ether as described infra. 3 µL of 1,2-Dipalmitoyl-L-3-phosphatidyl[N-methyl-$^3$choline was added as a lipid marker. The mixture was evaporated into a thin lipid film, which was hydrated with 3 mL of the modified UEA I or WGA solution obtained as described above. PBS was used instead when preparing lectin-free liposomes. The liposomes were freeze-thawed, extruded, and polymerized with the redox initiators $Na_2S_2O_5$ and $K_2S_2O_8$. The resulting polymerized liposomes were purified on a Biogel A 15M column. Fractions containing liposomes were identified by their turbid appearance and were collected. The final lipid concentration was adjusted to ~10 mg/mL.

XPS Analysis of lectin-bearing Liposomes

The presence of lectins on the liposome surface was confirmed using X-ray photoelectron spectroscopy (XPS). Lectin-bearing liposomes were prepared as described above. Droplets of the liposome suspensions were applied on a clean aluminum substrate. Once the water evaporated, a thin layer of liposomes was formed on the substrate. The surface chemical composition of the liposome layer was then examined using a Surface Science SSX-100 spectrometer.

In vitro Agqregation Assay for Immobilized Lectins

The carbohydrate binding activities and specificities of the immobilized lectins were examined in vitro using an aggregation assay. The substrate of UEA I or for WGA (see Table 1) was dissolved in PBS at different concentrations and 100 µL was added to suspensions of UEA I or WGA-modified liposomes (lipid concentration adjusted to ~1 mg/mL). The total volume was 1.5 mL. The mixtures were vortexed and incubated at 25° C. for 20 minutes and then transferred to the UV/VIS spectrometer. Liposome aggregation was followed by the turbidity (A450) increase of the suspensions. Carbohydrate specificity of the immobilized lectins was tested by incubating the lectin-bearing liposomes with 100 µmol of the inhibitors (Table 1) before the substrates were added.

TABLE 1

Substrates and inhibitors for in vitro aggregation assay

|  | UEA I | WGA |
| --- | --- | --- |
| Binding Specificity Substrate | 2'-fucosyllactosamine residues | N-acetyl-glucosamine residues |
|  | 2'-fucosyllactosamine HSA conjugate (Accurate Chemical & Scientific Corp., Westbury, NY) | Glycophorine (Sigma) |
| Inhibitor | L-fucose (Sigma) | N-acetyl-glucosamine (Sigma) |

In vivo Uptake of Liposomes

Three groups of four mice each were used to study and compare the in vivo uptake of UEA I liposomes, and WGA liposomes. All mice were fasted for 12 hours before the experiment but allowed free access to water. Mice from groups one and two were gavaged with 200 µL suspensions of UEA I liposomes or WGA liposomes, each using a 24 gauge ball-tipped gavage needle. The third group was given PBS only. They were used as a control for the experiment. Food was restored immediately after administration. At 2 hours post administration, the mice were anaesthetized and blood was sampled (Waynforth et al., 1992 Experimental and surgical technique in the rat. London: Academic Press. The mice were then sacrificed with carbon dioxide. Tissue samples (i.e, spleen, mesentery, liver, kidney, heart, lung, Peyer's patches, and patch-free intestine) were collected and treated as described infra. Dissolved tissue samples were then counted in the liquid scintillation counter.

9.2. RESULTS

Formation of Lectin-bearing Polymerized Liposomes

TNBS reacts with free amino groups in proteins and gives absorbance at 420 nm (Fields, 1971, Biochemistry Journal 124:581–590). Since the NGPE modification also takes place on the amino groups in the lectins, the TNBS assay is used to quantify the reduction in the number of amino groups during lectin modification. The relative decrease in $A_{420}$ measured for the same lectin before and after the reaction can be used to calculate the extent of lectin modification. A typical degree of modification obtained using this assay was between 40–70%.

XPS Analysis

Figure 5A:
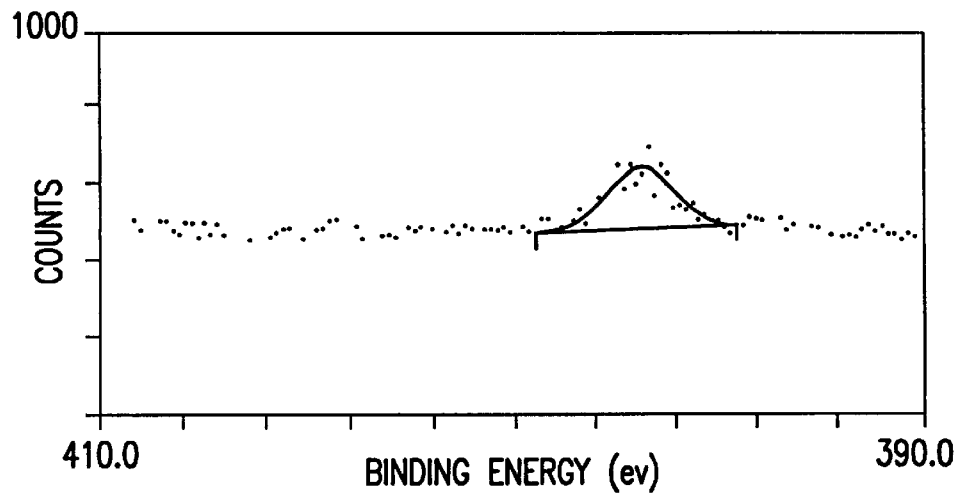
FIG. 5 shows high resolution X-ray photoelectron spectra on nitrogen for liposomes of different compositions: (A) lectin-free liposomes; (B) UEA modified liposomes; and (C) WGA modified liposomes.
Figure 5B:
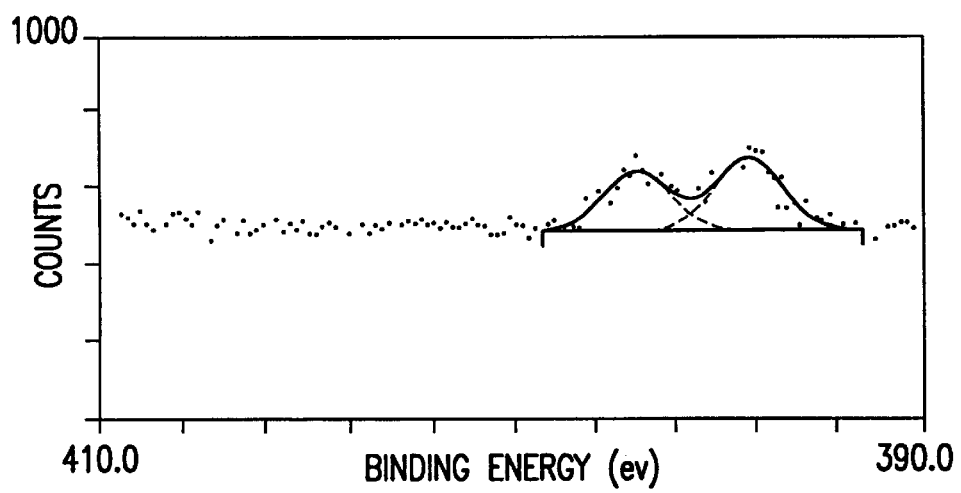
Figure 5C:
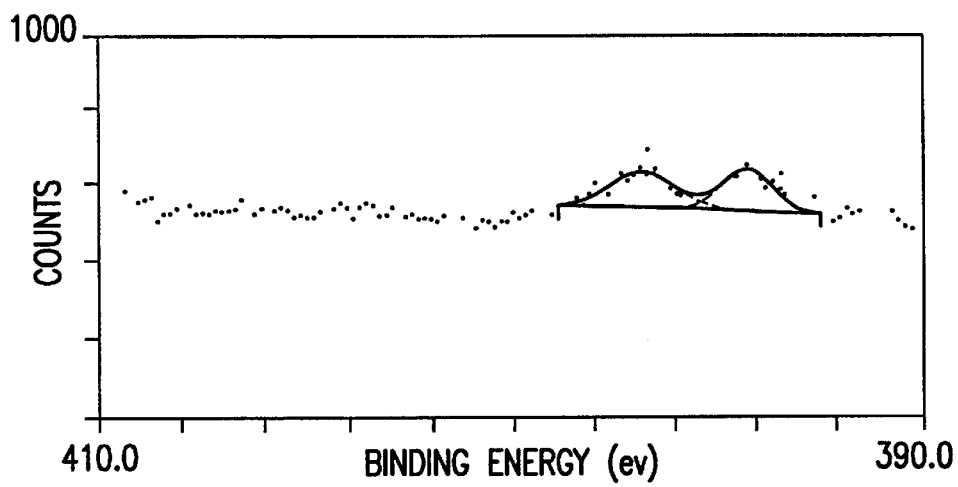

Both survey and high resolution XPS scans were used to confirm the presence of lectins on the liposome surfaces. A summary of the chemical compositions on the polymerized liposome surfaces is shown in Table 2. Carbon (C), oxygen (O), nitrogen (N), and phosphorous (P) were detected on the lectin-free liposomes, with the nitrogen to phosphorous atom ratio (N:P) very close to unity. In comparison, both UEA I liposomes and WGA liposomes shown an increased N:P ratio, implying the presence of nitrogen-rich molecule, (i.e., the lectins). In WGA-bearing liposomes, about 1.08% sulfur was also detected besides carbon, oxygen, nitrogen, and phosphorous. Since the only possible source of sulfur is the methionine or cysteine residues in the lectins, the sulfur detected proves the existence of WGA molecules on these liposome surfaces. Sulfur was not detected on UEA I liposomes, however, due to the low sulfur content (only one cysteine and one methionine out of 244 amino acids) in this lectin. To confirm the lectin presence on the UEA I modified liposomes, a high resolution scan for nitrogen was conducted. For the lectin-free liposomes (FIG. 5A), a single peak with binding energy of 397 eV was detected. UEA I liposomes, however, exhibited an extra peak with a slightly lower peak binding energy (364 eV) (FIG. 5B). This indicates the presence of a new type of nitrogen on the UEA I-modified liposomes. This new type of nitrogen gas a slightly different chemical environment than that of the original nitrogen in the phospholipids. This new nitrogen peak can only represent the nitrogen content from the UEA I molecules. A similar pattern was also seen for WGA liposomes as shown in FIG. 5C.

In vitro Aggregation

Figure 6:
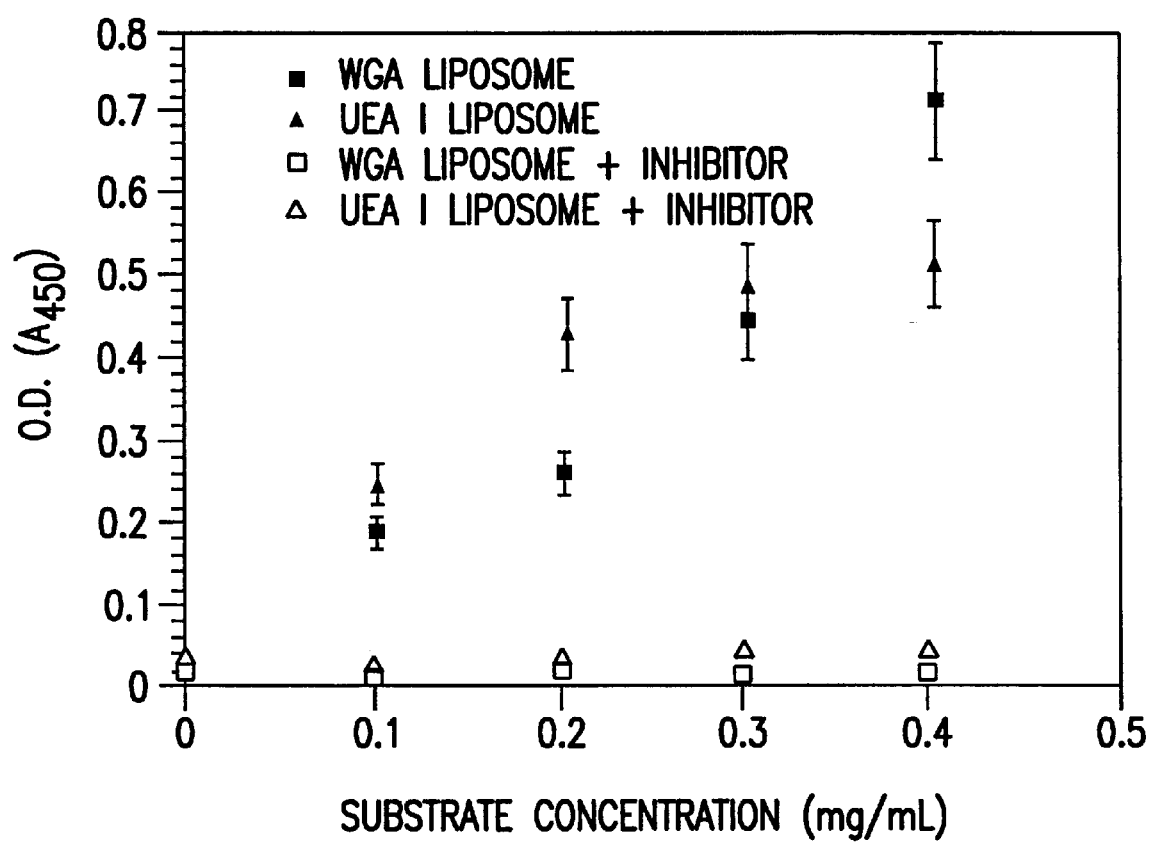
FIG. 6 shows in vitro aggregation of WGA and UEA liposomes in the presence of their substrates or inhibitors (Table 1). Each data point was an average of three measurements and the error bars were standard error.

Turbidity changes of the liposome suspensions in the presence of their corresponding substrates (Table 1) were plotted in FIG. 6. When substrates were added to lectin-bearing liposomes, the turbidity of the suspensions increased with increasing substrate concentration, indicating increased aggregation of the lectin-modified liposomes (FIG. 6). This establishes that the lectins maintained their binding activity after immobilization. In the presence of the inhibitors (Table 1), however, virtually no change in turbidity was observed, even when the same substrates were added (FIG. 6). Liposome aggregation caused by the binding substrates was effectively inhibited by the binding inhibitors (FIG. 6). This indicates that the carbohydrate specificity of these lectins remain unaltered after immobilization.

In vivo Uptake of Liposomes

No radioactivity was detected in the tissues when the mice were administered PBS. The amount of radioactivity retained in all other tissue samples was measured and were divided by the total activity administered to give the percent distribution of the radiolabel in each tissue. These percentages were then normalized with individual tissue sample weight to compensate for animal-to-animal variations. The normalized results are summarized in FIG. 7, together with the data obtained for lectin-free polymerized liposomes. Liposomes gave a significantly higher level of binding to Peyer's patches when their surfaces were modified with UEA I, without increasing-their binding to the regular intestinal epithelium (FIG. 7). WGA liposomes gave slightly stronger binding to the Peyer's patches than lectin-free liposomes. However, given WGA's equal affinity for all epithelial cells, it is also led to a higher binding level to the regular intestinal epithelium (FIG. 7). When lectin-containing liposomes were administered, a greater amount of radioactivity was detected in organs such as liver and kidney. UEA I liposomes showed ten times and WGA liposomes three times as much radioactivity in the liver when compared to liposomes that were not modified with any lectins. This implies an improved level of liposomal uptake from the agastrointestinal tract.

If an average weight is taken for each tissue, an overall bioavailability of the liposomes can be estimated (Table 3). Of the total amount of liposomes administered, ~3.2% lectin-free liposomes were taken up. Compared to the lectin-free liposomes, about twice as much (~5.8%) WGA liposomes and three times as much (~10.6%) UEA I liposomes were transported from the animal gastrointestinal tract into the circulation after a single dose oral administration. These latter two values are significantly higher than the lectin-free polymerized liposomes when they are examined using statistical (ANOVA) tests ($p<0.001$).

9.3. DISCUSSION

Lectins are non-membrane hydrophilic molecules. They can be incorporated into the liposome membranes by modifying them with a hydrophobic anchor, NGPE. During liposome formation, increased lipophilicity will force the hydrophobic tails to partition into the membrane phase and expose the lectins to the water phase (Weissig 1986 FEBS Letters 202:86–90).

The amount of liposome uptake in vivo was calculated from the amount of radioactivity found in the tissues. This was based on the previous observations that polymerized liposomes remain intact in mouse gastrointestinal tract, and the radioactive membrane markers stay tightly associated with the liposomes. As a result, the amount of radioactivity detected in the tissues can effectively represent the amount of intact liposomes taken up from the gastrointestinal tract.

Both types of lectin-modified liposomes gave a higher level of uptake, due to their increased Peyer's patch binding when compared with lectin-free liposomes. UEA I liposomes, however, gave the best delivery efficiency.

In this example, polymerized liposome surfaces were modified with lectin molecules (UEA I or WGA) in attempts to improve liposome delivery efficiency. It was shown that about 10.6% of the UEA I liposomes and 5.8% of the WGA liposomes were taken up from the gastrointestinal tract. These numbers are significantly higher than the 3.2% observed in the case of lectin-free liposomes. At the same time, UEA I liposomes exhibited the most effective Peyer's patch targeting among the three, which directly correlated with the highest delivery efficiency observed. This establishes that lectin modifications of liposomes can promote binding to Peyer's patches, which will give improved efficiency for Peyer's patch-targeted delivery.

10. ORAL DELIVERY OF DIPHTHERIA TOXOID VACCINES

Immunization of children with diphtheria toxoid is now almost universal in every developed country in the world, where except in rare instances diphtheria is almost completely eradicated. Table 4 shows the recommended immunization schedule provided by the American Immunization Practice Advisory Committee for children under 7 years of age (Pappenheimer 1984 in Bacterial Vaccines, Academic Press, Inc.: Orlando p 1–32). Usually, diphtheria toxoid is administered intramuscularly together with tetanus toxoid and B. pertussis vaccine (DTP).

It can be seen from Table 4 that repeated shots, both primary as well as boosters, are required to achieve a complete protection against the disease. In this case, patient compliance can be a major factor in determining the efficacy of the immunization. On the other hand, if an oral formulation can be used instead, it is not only more convenient, increased patient compliance is also expected.

In this study, diphtheria toxoid is encapsulated into lectin modified polymerized liposomes described infra and the immunogenicity of the formulation is tested in mice.

10.1. MATERIALS AND METHODS

Lectin modification

UEA I was derivatized with N-glutaryl-phosphatidylethanolamine as described infra. The modification product was dialyzed in a Spectrum® dialysis tube (MWCO 1,000) overnight against PBS (20 mM, pH7.6) in the presence of 50 mg Biobeads® to facilitate the removal of the detergent and other excess reagents. The final solution was stored at 4° C. until use.

Table 4. Routine immunization schedule for children less than 7 years of age.

| Dose | Age and interval |
|---|---|
| Primary 1 | 6 weeks or older |
| Primary 2 | 4–8 weeks after first dose |
| Primary 3 | 4–8 weeks after second dose |
| Primary 4 | ~1 year after third dose |
| Booster | 4–6 years old |
| Additional boosters | Every 10 years after last dose |

Formation of Diphtheria Toxoid-containing Liposomes 40 mg of DODPC was dissolved in chloroform and ethyl ether. The mixture was rotary-evaporated into a thin lipid film. The dried lipid was hydrated with 4 mL of the modified UEA I containing 1.5 mg/mL diphtheria toxoid (a gift from Dr. George Siber from Massachusetts State Laboratory, Jamaica Plain, Mass.). The liposomes obtained were freeze-thawed and extruded as described infra. When preparing empty liposomes as experimental controls, no diphtheria toxoid was added. Polymerization was carried out overnight at room temperature with redox initiators $Na_2S_2O_5$ and $K_2S_2O_8$. The resulting polymerized liposomes were purified on the Biogel A15M column with PBS as eluting buffer. The final lipid concentration was adjusted to ~10 mg/mL.

The diphtheria toxoid left unencapsulated in the liposome suspension was collected from the column and the amount was determined using a micro BCA protein assay (Pierce, Rockford, Ill.). Based on this number, the amount of diphtheria toxoid encapsulated in the liposomes was estimated. An equal amount of diphtheria toxoid was added to the empty liposomes prepared above, so that the final diphtheria toxoid concentrations in the empty liposomes preparation was identical to that of the diphtheria toxoid-containing liposomes.

In vivo Immunization

Two groups of six mice each were used in experiment. For the primary dose, mice from group one were each gavaged diphtheria toxoid-containing liposomes, and mice from group two were given the empty liposomes mixed with diphtheria toxoid. All mice were housed under normal conditions after dosing. A second dose was given to the mice two weeks after the primary dose. Blood samples were taken from cardiac puncture right before the primary dose, and at two weeks, four weeks, and eight weeks after the primary dose. Plasma was harvested after centrifugation of the blood samples and was stored at −70° C. till assay.

Enzyme-linked Immunoassay (ELISA)

The ELISA assay was conducted by collaborators at the Massachusetts State Laboratory, using a similar protocol as described elsewhere (Gupta et al., 1996, J. Infectious Disease 173:1493–1497). Briefly, 96-well plates (Dynatech Laboratories, Chantilly, Va.) were coated with diphtheria toxoid (100 μL at 5 μg/mL in PBS, pH 7.2) overnight at room temperature. Plates were then washed three times with PBS containing 0.05% Tween 20 (Sigma, St. Louis, Mo.). Plasma samples were applied to the plates in 2-fold steps using PBS with 0.1% Brij 35 (Sigma) and 0.5% bovine serum albumin as a diluent (PBB). After the plates were incubated for 2 hours at room temperature, Fc-specific alkaline phosphatase-conjugated goat anti-mouse IgG (Caltag Laboratories, San Francisco, Calif.) diluted in PBB was added to each well and the plates were incubated at room temperature for 2 hours. Finally, 1 mg/mL p-nitrophenyl phosphate (Sigma) in diethanolamine-$MgCl_2$ buffer was added to each well and the plates were read at 405 nm after 30 minutes using an ELISA plate reader (Titertek Multiskan, ICN Biomedicals, Costa Mesa, Calif.). The diphtheria toxoid antibody concentrations of the samples were calculated from a standard curve constructed using standards of known concentrations.

10.2. RESULTS

The liposomes were characterized as described infra. The amount of diphtheria toxoid encapsulated in the diphtheria toxoid-containing liposomes was determined to be 150 μg/mL in the final suspension. Therefore, about 150 μg/mL of diphtheria toxoid was added to the empty liposome suspension. This was used as one of the experimental controls.

The results from the ELISA were shown in Table 5 and FIG. 8 for the two liposome formulations administered. The antibodies detected were the total amount of anti-diphtheria toxoid Igs present in the plasma samples. Two mice died during the administration in each group, the other four survived till the end of the experiment. No antibodies were detected in any of the animals used before the oral administration (Table 5). After the primary dose, it can be seen that all of the four mice from group one who were give diphtheria toxoid-containing polymerized liposomes showed increases in their serum Ig levels, while no changes were seen for the four mice in group two who were given polymerized liposomes mixed with diphtheria toxoid (FIG. 8). This indicates that the polymerized liposomes can provide protection to the diphtheria toxoid, but only if the vaccines are incorporated within the liposomes. Simple mixing of diphtheria toxoid with the polymerized liposomes is not sufficient to provide protection to the vaccines against degradation. Also, when encapsulated inside the polymerized liposomes, diphtheria toxoid remains active and that a single dose of the formulation is effective to induce immune responses.

After the second dose, three of the four mice from group one displayed sustained increases of their serum Ig levels, although one of the animals failed to respond to the second dose and its Ig level dropped to the baseline after 4 weeks (FIG. 8). Previous studies suggested that a minimal Ig level of 0.5 μg/mL is required for protection (Gupta et al., 1996, J. Infectious Disease 173:1493–1497). Therefore, three out of the four mice in the first group have acquired toxin neutralizing abilities through oral immunization. None of the mice from group two showed any changes in their Ig levels, even after the second dose. The diphtheria toxoid-containing polymerized liposomes cannot only induce primary responses, but secondary responses as well.

As an additional control for the experiment, mice were also given diphtheria toxoid in PBS. No serum Igs were detected in these mice.

These results clearly indicated that the diphtheria toxoid-containing polymerized liposomes are able to induce good systemic immune responses, as shown by the serum antibody levels in mice.

Table 5 Serum anti-diphtheria antibody levels detected in mice after oral administration of diphtheria toxoid encapsulated in polymerized liposomes or diphtheria mixed with polymerized liposomes.

| | | Serum Igs (μg/mL) | | | |
|---|---|---|---|---|---|
| Sample administered | Animal ID | 0 weeks | 2 weeks | 4 weeks | 8 weeks |
| Group 1: | mouse #1 | 0.03 | 3.34 | 6.42 | 61.40 |
| Polymerized liposomes | mouse #2 | 0.03 | 2.30 | 0.03 | 0.11 |
| with diphtheria toxoid | mouse #3 | 0.03 | 35.87 | 54.96 | 356.14 |
| incorporated | mouse #4 | 0.03 | 1.70 | 2.25 | 5.62 |
| Group 2: | mouse #1 | 0.03 | 0.03 | 0.03 | 0.03 |
| Polymerized liposomes | mouse #2 | 0.03 | 0.03 | 0.03 | 0.03 |
| mixed with diphtheria | mouse #3 | 0.03 | 0.03 | 0.03 | 0.03 |
| toxoid | mouse #4 | 0.03 | 0.03 | 0.03 | 0.06 |

11. EXAMPLE: ORAL DELIVERY OF INSULIN

In this study, the possibility of using lectin modified polymerized liposomes to delivery other biologically active peptides and proteins is explored using insulin as a model compound.

11.1. MATERIALS AND METHODS

Lectin modification

UEA I was derivatized with N-glutaryl-phosphatidylethanolamine as described in infra. The modification product was dialyzed in a Spectrum® dialysis tube (MWCO 1,000) overnight against PBS (20 mM, pH7.6) in the presence of 50 mg Biobeads® to facilitate the removal of the detergent and other excess reagents. The final solution was stored at 4° C. until use.

Formation of Insulin-containing Liposomes 30 mg of DODPC was dissolved in chloroform and ethyl ether. The mixture was rotary-evaporated into a thin lipid film. The dried lipid was hydrated with 3 mL of the modified UEA I containing, 58 IU/mL human insulin (regular, purchased from MIT Pharmacy). Insulin in PBS was used instead when preparing UEA I-free liposomes. The liposomes obtained were freeze-thawed and extruded as described infra. Polymerization was carried out $Na_2S_2O_5$ and $K_2S_2O8$. No initiators were used when unpolymerized liposomes were prepared. The resulting polymerized liposomes were purified on the Biogel A15M column (Chapter 3) with PBS as eluting buffer. The final lipid concentration was adjusted to ~10 mg/mL.

The insulin left unencapsulated in the liposomes was collected from the column and the amount was determined using a radio-immuno-assay (RIA) Based on this number, the entrapment efficiency of the insulin was determined.

In vivo Insulin Delivery

Balb/C mice of female sex were fasted for 12 hours before experiment. Each mouse was gavaged 200 μL of each preparation as described in Table 9.3. Food was restored immediately after administration. Blood samples for glucose determination was drawn from mouse tail vein under methoxyflurane anesthesia. Samples were drawn right before the administration (O hour), as well as at 1, 2, 3 and 3.5 hours post administration of each preparation. Blood glucose level was measured using a One Touch® Profile Diabetes Tracking System (Lifescan, Milpitas, Calif.) with One Touch® Test strips, by applying blood to form a round drop which completely covered the test spot on the test strip. Readings (in mg/dL) were obtained from the meter indicating the blood glucose level detected.

11.2. RESULTS

The liposomes were characterized as described infra. The amount of insulin encapsulated in the liposomes was determined using the RIA assay (performed by Linco Research, St. Charles, Mo.) to be about 5 IU/mL of liposome suspension.

Blood glucose level at zero hour was taken at 100 percent. Blood glucose levels after the oral administration were normalized by the level at zero hour, and the results were plotted in FIG. 9. It can be seen that when administered in solution, insulin did not result in any significant change in mouse blood glucose levels (FIG. 9). This was due to the degradation of the unprotected peptide in the gastrointestinal tract by the digestive enzymes. When insulin was encapsulated in unpolymerized liposomes, no drop in blood glucose level was observed (FIG. 9), suggesting that the unpolymerized liposomes were not able to protect the encapsulated insulin from degradation. This is consistent with the fact that unpolymerized liposomes are not stable in the gastrointestinal tract, where they are dissolved by the biological detergents. The dissolution results in the exposure of liposomal contents and therefore the loss of liposome protective functions. PBS was also administered to the mice as an experimental control. No significant-decrease was observed in the blood glucose levels (data not shown).

When insulin was encapsulated into the liposomes and the liposomes were subsequently stabilized through polymerization, a significant decrease in blood glucose level (to ~70% of original) was observed at two hours post administration (FIG. 9). Furthermore, when the polymerized liposomes were surface-modified with UEA I molecules, which were shown to target the liposomes to Peyer's patches and give improved oral delivery efficiency, the blood glucose dropped—40% compared to the original level at 3 hours post administration (FIG. 9). In both cases, no significant change in the glucose level was observed at one hour after the administration. This lag time is due to the gastric and intestinal transit time of these liposomes.

The results of these studies demonstrate the efficacy of lectin modified polymerized liposomes to provide protection for diphtheria toxoid as well as insulin. Both peptides retained their biological activity after the encapsulation and polymerization process. When orally administered to mice, both peptides displayed their desired biological responses. Lectin modified polymerized liposome encapsulated diphtheria toxoid was shown to induce both primary and secondary immune responses in mice and lectin modified polymerized liposome encapsulated insulin was shown to reduce blood glucose levels in mice. These results demonstrate that polymerized liposomes of the invention can be used as delivery systems.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

We claim:

1. A polymerized liposome suitable for oral delivery of a biologically active substance comprising a phospholipid bilayer having covalently bound phospholipids, an aqueous core and a bioactive molecule, wherein said liposome is modified to contain a targeting molecule which is selected from the group consisting of glycoproteins, lectins, carbohydrates, bacterial proteins and viral proteins.

2. The polymerized liposomes of claim 1 further comprising a vaccine, an antigen, biologically active drugs and detectable molecules.

3. The polymerized liposome of claim 1 wherein the targeting molecule is a lectin.

4. The liposomes of claim 1 wherein the biologically active substances are selected from the group consisting of cells, viruses, vectors, proteins, peptides nucleic acids, polysaccharides and carbohydrates, lipids, glycoproteins, and combinations thereof, and synthetic organic and inorganic drugs exerting a biological effect when administered to an animal.

5. The polymerized liposomes of claim 4 wherein the biologically active substance is an antigen.

6. The polymerized liposomes of claim 5 wherein the antigen is influenza hemeagglutinin.

7. The polymerized liposomes of claim 5 wherein the antigen is the ospA antigen from Lyme disease bacteria.

8. The polymerized liposomes of claim 5 wherein the antigen is a fragment of diphtheria toxin.

9. The polymerized liposomes of claim 1 having a degree of crosslinking between 30 and 100 percent.

10. The polymerized liposomes of claim 1 comprising phospholipids selected from the group consisting of double bond-containing olefinic and acetylenic phospholipids and phospholipids containing thiol groups.

11. The polymerized liposomes of claim 1 having a diameter of between fifteen nm and ten microns.

12. A pharmaceutical composition suitable for oral delivery which comprises a polymerized liposome of claim 1 and a pharmaceutically acceptable excipient or carrier suitable for oral delivery.

13. The polymerized liposome of claim 1 wherein the targeting molecule is covalently bonded to said polymerized liposome.

14. A method of orally delivering molecules to an animal which comprises administering to said animal polymerized liposomes comprising a phospholipid bilayer having covalently bonded phospholipids, an aqueous core, a targeting molecule selected from the group consisting of glycolproteins, lectins, carbohydrates, bacterial proteins and viral proteins and a bioactive molecule.

15. The method of claim 14 wherein the biologically active substance is a detectable compound selected from the group consisting of radiopaque substances, air, magnetic materials, and substances detectable by magnetic resonance imaging.

16. The method of claim 14 wherein the molecules are biologically active substances selected from the group consisting of cells, viruses, vectors, proteins, peptides, nucleic acids, polysaccharides and carbohydrates, lipids, glycoproteins, and combinations thereof, and synthetic organic and inorganic drugs exerting a biological effect when administered to an animal.

17. The method of claim 14 wherein the biologically active substance is an antigen and the liposomes are administered to the animal in an amount effective to elicit a humoral or cell mediated immune response against the antigen.

18. The method of claim 14 further comprising providing an adjuvant in the hydrophobic layer of the liposome.

* * * * *